(12) United States Patent
Whibbs et al.

(10) Patent No.: US 8,538,779 B1
(45) Date of Patent: *Sep. 17, 2013

(54) METHOD AND SYSTEM FOR ONLINE SECURE PATIENT REFERRAL SYSTEM

(75) Inventors: Vinnie Whibbs, Pensacola, CA (US); E. Coy Irvin, Pensacola, FL (US); Ellis W. Bullock, III, Pensacola, FL (US)

(73) Assignee: Scheduling.com, Inc., Campbell, CA (US)

( * ) Notice: Subject to any disclaimer, the term of this patent is extended or adjusted under 35 U.S.C. 154(b) by 825 days.

This patent is subject to a terminal disclaimer.

(21) Appl. No.: 12/729,289

(22) Filed: Mar. 23, 2010

Related U.S. Application Data

(63) Continuation of application No. 11/152,724, filed on Jun. 14, 2005, now Pat. No. 7,702,524, which is a continuation-in-part of application No. 10/869,809, filed on Jun. 16, 2004, now abandoned.

(60) Provisional application No. 60/478,933, filed on Jun. 16, 2003.

(51) Int. Cl.
G06Q 10/00 (2012.01)
G06Q 50/00 (2012.01)

(52) U.S. Cl.
USPC .................................................. 705/3; 705/2

(58) Field of Classification Search
USPC ......................................................... 705/2, 3
See application file for complete search history.

(56) References Cited

U.S. PATENT DOCUMENTS

| | | | |
|---|---|---|---|
| 5,579,393 A * | 11/1996 | Conner et al. | 713/176 |
| 5,918,208 A * | 6/1999 | Javitt | 705/2 |
| 6,263,330 B1 | 7/2001 | Bessette | |
| 6,466,133 B1 * | 10/2002 | Skardon | 340/627 |
| 6,651,060 B1 * | 11/2003 | Harper et al. | 1/1 |
| 6,734,886 B1 * | 5/2004 | Hagan et al. | 715/853 |
| 6,915,265 B1 * | 7/2005 | Johnson | 705/2 |
| 8,392,214 B1 * | 3/2013 | Pinsonneault | 705/2 |
| 2001/0053986 A1 * | 12/2001 | Dick | 705/3 |
| 2002/0010679 A1 * | 1/2002 | Felsher | 705/51 |
| 2002/0016923 A1 | 2/2002 | Knaus et al. | |
| 2002/0116227 A1 * | 8/2002 | Dick | 705/3 |
| 2002/0161606 A1 * | 10/2002 | Bennett et al. | 705/2 |
| 2003/0050803 A1 | 3/2003 | Marchosky | |
| 2006/0047537 A1 * | 3/2006 | Brimdyr | 705/2 |
| 2009/0150292 A1 * | 6/2009 | Trinh et al. | 705/55 |

* cited by examiner

*Primary Examiner* — Neal Sereboff
(74) *Attorney, Agent, or Firm* — Christine Q. McLeod; Beusse, Wolter, Sanks, Mora & Maire, P.A.

(57) ABSTRACT

The present invention provides a system and method, relating to the transfer of patient files over a secure, HIPAA compliant, patient file transfer and outpatient order system and a computer site therefore. The method includes obtaining and compiling a patient record pertaining to a patient; electronically inputting the patient record obtained into a secure computer database containing other patient records, allowing physician access to the patient record wherein the access includes allowing the physician to order outpatient services and send part of the patient information, including certain defined fields for a complete record and to send and receive referrals including certain defined fields for a complete record.

20 Claims, 40 Drawing Sheets

| Referral Dashboard | Lab Dashboard |                                    Welcome Back Main Desk, Primary Demo | Logout eFileShare News                                    (more news)

ⓘ NEW FEATURE – EASIER ORDER ENTRY FOR HOSPITAL TESTS
Based on feedback from system users we have added a checkbox ability for specific tests & CPT codes in the following categories...

Beau Rivage
Resort & Casino – Biloxi
NEW EFILE SHARE USER CONTEST MAY 2003
Win a $500 Gift Certificate to the Beau Rivage Resort in Biloxi, Mississippi...

Billy-Bob's BEACH BARBECUE
April Contest – Office Competition
*THE RESULTS ARE IN*
Here are the winners from the April Contest – (stay tuned for our next contest which should start next week).

eFile Share Members FAQ's                         (more faq's)

ⓘ When Do Referrals get Removed from the Dashboard?
The referrals are removed as follows...

ⓘ How Does the Status "Follow-Up" Work?
After a referral has been archived if either office needs to send the other office additional information you can now do so...

When Should I Use "ACCEPTED?"
The "ACCEPT" status should now ONLY be used for information transfers...

How does the Scheduled status work?

Are the Diagnosis Notes and Codes Required?
Yes – due to a lot of requests from users we have made the diagnosis notes and codes fields required...

Featured eFileShare Member                        (more features)

West Florida HEALTHCARE
New Member – West Florida Hospital
You can now order West Florida Hospital tests using eFileShare...

Featured eFileShare Member                        (more features)

Jeffrey B. Comitalo, M.D., FACS
New Member – Jeffrey B. Comitalo, M.D., FACS
eFileShare is happy to welcome Jeffery B. Comitalo, M.D., FACS to the greater Pensacola eFileShare community...

Pharmacare Group
New Member – Pharmacare
eFileShare is happy to welcome Pharmacare to the greater Pensacola eFileShare community...

New Member – Hermatology/Oncology Associates:
eFileShare is happy to welcome Hematology/Oncology Associates to the greater Pensacola eFileShare community...

New Member – Coastal Medical Equipment & Supplies
eFileShare is happy to welcome Coastal Medical Equipment & Supplies to the greater Pensacola eFileShare community...

HMSS
Home Medical Supply Solutions
New Member – Home Medical Supply Solutions, Inc.
eFileShare is happy to welcome Home Medical Supply Solutions, Inc. to the greater Pensacola eFileShare community

New Member – Comfort-n-Mobility (DME)
eFileShare is happy to welcome Comfort-n-Mobility to the greater Pensacola eFileShare community...

Sacred Heart Women's Hospital
New Member – Sacred Heart Medical Group – Pensacola Blvd. Office
eFileShare is happy to welcome the Sacred Heart Medical Group – Pensacola Blvd. team to the greater Pensacola eFileShare community...

West Florida HEALTHCARE
New Member – West Florida Behavioral Health
eFileShare is happy to welcome West Florida Behavioral Health to the greater Pensacola eFileShare community...

Sacred Heart Women's Hospital
New Member – Regional Perinatal Center
eFileShare is happy to welcome the Regional Perinatal Center at Sacred Heart's Women's Hospital to the greater Pensacola eFileShare community...

Eduardo Puente, M.D.
Diplomat, American Board of Urology
New Member – Dr. Eduardo Puente – Urology
eFileShare is happy to welcome Dr. Eduardo Puente to the greater Pensacola eFileShare community...

*FIG. 3c*

| Referral Dashboard | Lab Dashboard | Create Referral | Search Referrals |   Welcome Back Specialist Demo Main Desk I Logout Incoming Referrals                                                                                  Legend  Help

|   | Status | Status   | To                                  | From                                      | Status Date/Age                       | ✉   |
|---|--------|----------|-------------------------------------|-------------------------------------------|---------------------------------------|-----|
| ⓘ | SENT   | Doe, John| Plugit-Specialist Wirth, James MD   | Plugit-Primary Care Test Keith Nicholson MD | 5/22/2003 10:16:36 AM 0 Day(s) 0 Hours | 0/0 |

Outgoing Referrals                                                                                  Legend  Help

|   | Status | Status   | To                                        | From                                | Status Date/Age                       | ✉   |
|---|--------|----------|-------------------------------------------|-------------------------------------|---------------------------------------|-----|
| ⓘ | SENT   | Doe, John| Plugit-Primary Care Test Keith Nicholson MD | Plugit-Specialist Wirth, James MD | 5/22/2003 10:18:41 AM 0 Day(s) 0 Hours | 0/0 |

Legend

✉  Correspondence
   New Correspondence/All Correspondence
   Click this link to see correspondence
   attached to this referral.

ⓘ  Urgent
   This referral needs your immediate
   attention. This applies to new referrals
   and referrals with new messages.

ⓘ BOLD  STAT Referral
   This patient must be seen within
   72 hours!

A↓Z  Click on any column title to sort by
   that column.

LATE  Nothing has been done with this order
   in 5 days. You should click in and
   change the status.

FIG. 3d

| Referral Dashboard | Lab Dashboard | Create Referral | Search Referrals |   Welcome Back Specialist Demo Main Desk I Logout Add Correspondence To:       Baptist Hospital (Gulf Breeze)
          Baptist Physician
From:     Specialist Demo Main Desk
Message:  [                    ]

[Submit] [Cancel]

FIG. 3f

| Referral Dashboard | Lab Dashboard | Create Referral | Search Referrals | Welcome Back Specialist Demo Main Desk I Logout |

Change To   Cancel                                                      Add Document  Add Correspondence  Print

Referral Information                          Patient Information
From Group:     Plugit – Specialist              Name:            Doe, John
From Doctor:    Wirth, James MD                  SSN:             555555555
To Group:       Baptist Hospital (Gulf Breeze)   Address:         2211 Biasden
To Doctor:      Baptist Physician                                 Pensacola, FL 32503
To Specialty:   CT                               Home Phone:      888-888-8888
Scheduling:     Please call patient for appointment   Work Phone:  999-999-9999
Referral Number: 4444444444                      Date of Birth:   07/04/1970
Expires:        1/1/2010                         Height:          5'11"
Number Visits:  5                                Weight:          170
Originator:     Specialist Demo Main Desk        Primary Insurance: BC/BS of Florida
Created:        5/22/2003 10:33:08 AM                             XJG55555555555
                                                 Secondary Insurance: Beech Street
Status                                                        eeeeeee
Current Status: SENT                                              eeeeeee
Sent:           5/22/2003 10:33:08 AM            Signature on File: NO
Received:
Responded:
Archived:

Diagnosis                     [signature]  5/22/2003 10:33:08 AM
Diagnosis Codes: 123.4, 456.7, 891.1, 521.4
Sample Diagnosis Notes

Test Required
Sample Other Test Required

Requested Tests
72125 CT SCAN, CERVICAL SPINE; W/O CONTRAST
74150 CT SCAN, ABDOMEN; W/O CONTRAST

Other Notes
Sample Other Notes

Attached Documents

| Filename | Description | Date | Action |
|---|---|---|---|
| Employee Extensions(1).doc | Sample upload patient file | 5/22/2003 10:33:08 AM | Open I Remove |

*You can only remove files that you uploaded.

Correspondence

| To | From | Sent | Received Message** |
|---|---|---|---|
| Baptist Hospital (Gulf Breeze) | Specialist Demo Main Desk | 5/22/2003 10:36:00 AM | Testing correspondence feature |

**Click message to read.

*FIG. 3e*

| Referral Dashboard | Lab Dashboard | Create Referral | Search Referrals |  Welcome Back Main Desk Primary Demo I Logout Archive                                              Add Document  Add Correspondence  Print Referral Information                    Patient Information
From Group:      Plugit – Primary Care       Name:             Doe, John
From Doctor:     Test Keith Nicholson MD     SSN:              555555555
To Group:        Plugit – Specialist         Address:          2211 Biasden
To Doctor:       Wirth, James MD                               Pensacola, FL 32503
To Specialty:    Family Practice/Primary Care Home Phone:      888-888-8888
Scheduling:      Please call patient for appointment  Work Phone:  999-999-9999
Referral Number: 55555555                    Date of Birth:    07/04/1970
Expires:         1/1/2003                    Height:           5'11"
Number Visits:   6                           Weight:           170
Originator:      Main Desk, Primary Demo     Primary Insurance: BC/BS of Florida
Created:         5/22/2003 10:16:36 AM                          XJG55555555555
                                             Secondary Insurance: Beech Street
Status                                                          eeeeeee
Current Status:  ACCEPTED                                       eeeeeee
Sent:            5/22/2003 10:16:36 AM       Signature on File: NO
Received:        5/22/2003 10:25:08 AM
Responded:       5/22/2003 10:52:00 AM
Archived:

Diagnosis
Diagnosis Codes: 1111....                    [signature] 5/22/2003 10:16:36 AM
Test Requested Tests
Attached Documents

| Filename | Description | Date | Action |
| Employee Extensions.doc | Test | 5/22/2003 10:16:27 AM | Open I Remove |

*You can only remove files that you uploaded.

Correspondence

| To | From | Sent | Received Message** |
| Plugit – Primary Care | Specialist Demo Main Desk | 5/22/2003 10:26:00 AM | ⓘ Testing correspondence feature |

**Click message to read.

*FIG. 3g*

| Referral Dashboard | Lab Dashboard | Create Referral | Search Referrals |     Welcome Back Main Desk Primary Demo | Logout     | Start New Referral |
|---|---|---|---|---|---|

1. Start    2. Patient    3. Select Office    4. Add Document    5. Preview and Send

1. Start

Social Security Number*: [            ]
Ex. 555-55-5555 or 555555555

Priority*: [Normal ▽]

Scheduling*: [Please call patient for appointment ▽]

Referral Authorization Number*: [            ]

Authorization Expires*: [    ] / [    ] / [    ]
mm/dd/yyyy ex: 01/05/2003

Number of Visits: [    ]

Specialty*:
- Allergy and Immunology
- Cardiology
- Cath Lab
- Chiropractors
- CT
- Dermatology
- Dexascan
- Endocrinology/Metabolism

[Next →]

*Required Field

| Referral Dashboard | Lab Dashboard | Create Referral | Search Referrals |   Welcome Back Main Desk Primary Demo | Logout 1. Start   2. Patient   3. Select Office   4. Add Document   5. Preview and Send       Start New Referral 3. Select Office From Doctor*: Plugit – Primary Care – Test Keith Nicholson MD
Plugit – Primary Care – Wirth, James MD Click to select To Doctor*: Gastroenterology Associates (Baptist Division) – Baptist Physician
Gastroenterology Associates (Sacred Heart Division) – Adkisson, Wayne MD
Gastroenterology Associates (Sacred Heart Division) – Fineli, Scott MD
Gastroenterology Associates (Sacred Heart Division) – Haynes, Norman MD
Gastroenterology Associates (Sacred Heart Division) – Hakim, Fares MD
Gastroenterology Associates (Sacred Heart Division) – Orth, Roger MD
Gastroenterology Associates (Sacred Heart Division) – Smith, James MD
Medical Center Clinic – Gastroenterology – Calvit, Thomas MD Click to select Market: My Default Market Diagnosis Codes*: 123 , 456 , 789 , [ ] , [ ]
Click here for ICD-9 Code Listing
Separate multiple diagnosis codes with a comma Diagnosis Notes*: Insert diagnosis notes here Other Notes*: Other notes go here Tests        Test Description:
(!) Check the appropriate test box OR type the test required in the box beneath the test list ☐ 46390    COLONOSCOPY, FLEXIBLE, PROXIMAL TO SPLENIC FLEXURE, W/BX, SINGLE/MULTIPLE

☐ 43269    UPPER GI ENDOSCOPY; W/ENDOSCOPIC ULTRASOUND

☐ 43269    ENDOSCOPIC RETROGRADE CHOLANGIOPANCREATOGRAPHY; W/DESTRUCTION, LITHOTRIPSY, STONE, ANY METHOD

Test Required: [                    ]

Doctor Signature Required: ☑

[ Next → ]
*Required Field

*FIG. 3j*

| Referral Dashboard | Lab Dashboard | Create Referral | Search Referrals |  Welcome Back Main Desk Primary Demo | Logout 1. Start   2. Patient   3. Select Office   | 4. Add Document |   5. Preview and Send        Start New Referral 4. Add Documents
You may attach as many documents as needed to this referral below.
Once you have finished adding documents, Click "Next →" to preview this referral

| Next → |

Upload Documents
  Document: [                    ] | Browse |
  Description: [            ]
       From:   Main Desk, Primary Demo
              | Add Document |

FIG. 3k

| Referral Dashboard | Lab Dashboard | Create Referral | Search Referrals |  Welcome Back Main Desk Primary Demo | Logout 1. Start   2. Patient   3. Select Office   | 4. Add Document |   5. Preview and Send        Start New Referral 4. Add Documents
You may attach as many documents as needed to this referral below.
Once you have finished adding documents, Click "Next →" to preview this referral

| Next → |

Upload Documents
  Document: [F: \Employee Extensions.doc] | Browse |
  Description: [Sample patient file]
       From:   Main Desk, Primary Demo
              | Add Document |

FIG. 3m

| Referral Dashboard | Lab Dashboard | Create Referral | Search Referrals |   Welcome Back Main Desk Primary Demo I Logout |
|---|---|---|---|---|

1. Start   2. Patient   3. Select Office   | 4. Add Document |   5. Preview and Send     Start New Referral

4. Add Documents
You may attach as many documents as needed to this referral below.
Once you have finished adding documents, Click "Next →" to preview this referral

[ Next → ]

Attached Documents

| Filename | Description | Date | Action |
|---|---|---|---|
| Employee Extensions(2).doc | Sample Patient File | 5/22/2003 11:17:42 AM | Open I Remove |

Upload Documents

Document: [              ] [ Browse ]
Description: [              ]
From:  Main Desk, Primary Demo
[ Add Document ]

*FIG. 3n*

| Referral Dashboard | Lab Dashboard | Create Referral | Search Referrals |   Welcome Back Main Desk Primary Demo I Logout 1. Start   2. Patient   3. Select Office   | 4. Add Document |   5. Preview and Send      Start New Referral 4. Add Documents
You may attach as many documents as needed to this referral below.
Once you have finished adding documents, Click "Next →" to preview this referral
| Next → |

Attached Documents

| Filename | Description | Date | Action |
| --- | --- | --- | --- |
| Employee Extensions(2).doc | Sample Patient File | 5/22/2003 11:17:42 AM | Open I Remove |

Upload Documents
Document: [          ] [Browse]
Description: [          ]
From: Main Desk, Primary Demo
[Add Document]

*FIG. 3o*

| Referral Dashboard | Lab Dashboard | Create Referral | Search Referrals |   Welcome Back Main Desk Primary Demo I Logout Referrals Successfully Sent!
Review Referral I Create a New Referral I Home

*FIG. 3q*

| Referral Dashboard | Lab Dashboard | Create Referral | Search Referrals |  Welcome Back Main Desk Primary Demo | Logout |

1. Start   2. Patient   3. Select Office   4. Add Document   | 5. Preview and Send |   Start New Referral > 5. Preview and Send
> Referral is ready to be sent!
> | Send This Referral |

Referral Information
From Group:      Plugit – Specialist
From Doctor:     Wirth, James MD
To Group:        Gastroenterology Associates (Baptist Division)
To Doctor:       Baptist Physician
To Specialty:    Gastroenterology
Scheduling:      Please call patient for appointment
Referral Number: 55555555
Expires:         1/1/2003
Number Visits:   6
Originator:      Main Desk, Primary Demo
Created:         5/22/2003 1:05:09 PM

Diagnosis
Diagnosis Codes:   111, 222, 333, 444, 555
Sample Diagnosis Notes

Test Required
Other Test Required

Patient Information
Name:              Doe, John
SSN:               555555555
Address:           2211 Biasden
                   Pensacola, FL 32503
Home Phone:        888-888-8888
Work Phone:        999-999-9999
Date of Birth:     07/04/1970
Height:            5'11"
Weight:            170
Primary Insurance: BC/BS of Florida
                   XJG55555555555
                   123456
Secondary Insurance: Beech Street
                     eeeeeee
                     eeeeeee
Signature on File:   False

Requested Tests
46390    COLONOSCOPY, FLEXIBLE, PROXIMAL TO SPLENIC FLEXURE, W/BX,
         SINGLE/MULTIPLE
43269    UPPER GI ENDOSCOPY; W/ENDOSCOPIC ULTRASOUND
43269    ENDOSCOPIC RETROGRADE CHOLANGIOPANCREATOGRAPHY;
         W/DESTRUCTION, LITHOTRIPSY, STONE, ANY METHOD

Other Notes
Sample Other Notes

Attached Documents

| Filename | Description | Date | Action |
|---|---|---|---|
| Employee Extensions(3).doc | Sample upload patient file | 5/22/2003 1:06:04 PM | Open | Remove |

*FIG. 3p*

| Referral Dashboard | Lab Dashboard | Create Referral | Search Referrals |   Welcome Back Specialist Demo Main Desk | Logout Schedule Patient Appointment Doe, John
2211 Biasden
Pensacola, FL 32503
888-888-8888
999-999-9999

From:
Plugit – Primary Care
Test Keith Nicholson MD
To:
Wirth, James MD

◉ Patient has been notified.
○ Patient has not been notified.

Scheduling Note (required)

[Submit] [Cancel]

FIG. 3s

| Referral Dashboard | Lab Dashboard | Create Referral | Search Referrals |   Welcome Back Specialist Demo Main Desk | Logout Add Rejection Message NOTE: You cannot undo a rejection once the process is complete!

To:     Plugit – Primary Care
        Test Keith Nicholson MD
From:   Main Desk, Primary Demo
Message:

[Submit] [Cancel]

FIG. 3u

| Referral Dashboard | Lab Dashboard | Create Referral | Search Referrals |   Welcome Back Specialist Demo Main Desk I Logout Markets    Groups & Doctors    Office Staff    Insurance Providers Search Groups and Doctors (by Group, by Market, by Doctor Name)

Office Group: SHOW ALL
A Lab Not Specified
Baptist FirstRehab (9th Avenue)
Baptist FirstRehab (Gulf Breeze)
Baptist FirstRehab (Navarre)
Baptist FirstRehab (Pace)
Baptist FirstRehab (Westside)
Baptist FirstRehab – Baptist Hospital (Pensacola)
Baptist FirstRehab – Baptist Medical Park (9 Mile)
Baptist Hospital (Gulf Breeze)

Specialty: SHOW ALL
Allergy and Immunology
Cardiology
Cath Lab
Chiropractors
CT
Dermatology
Dexascan
Endocrinology/Metabolism

[Submit]  [Print]

*FIG. 3w*

| Referral Dashboard | Lab Dashboard | Create Referral | Search Referrals |   Welcome Back Specialist Demo Main Desk I Logout Markets    Groups & Doctors    Office Staff    Insurance Providers Doctor Search Results

| Group | City | State | Phone 1 | Phone 2 | Fax |
|---|---|---|---|---|---|
| Baptist FirstRehab (9th Avenue) | | | 850-478-7325 | | |
| Baptist Physician | Physical Therapy/Occupational Therapy | | | | |
| Baptist FirstRehab (Gulf Breeze) | | | 850-931-2181 | | |
| Baptist Physician | Physical Therapy/Occupational Therapy | | | | |
| Baptist FirstRehab (Navarre) | | | 850-593-1017 | | |
| Baptist Physician | Physical Therapy/Occupational Therapy | | | | |
| Baptist FirstRehab (Pace) | | | 850-994-6318 | | |
| Baptist Physician | Physical Therapy/Occupational Therapy | | | | |
| Baptist FirstRehab (Westside) | | | 850-453-8549 | | |
| Baptist Physician | Physical Therapy/Occupational Therapy | | | | |
| Baptist FirstRehab - Baptist Hospital (Pensacola) | | | 850-869-7555 | | |
| Baptist Physician | Physical Therapy/Occupational Therapy | | | | |
| Baptist FirstRehab - Baptist Medical Park (9 Mile) | | | 850-208-6120 | | |
| Baptist Physician | Physical Therapy/Occupational Therapy | | | | |
| Baptist Hospital (Gulf Breeze) | | | 850-469-7040 | | |
| Baptist Physician | CT | | | | |
| Baptist Physician | Dexascan | | | | |
| Baptist Physician | Mammography | | | | |
| Baptist Physician | MRI | | | | |
| Baptist Physician | Nuc Medicine | | | | |
| Baptist Physician | Radiology/Diagnostic Imaging | | | | |
| Baptist Physician | Ultrasound | | | | |
| Baptist Hospital (Pensacola) | Pensacola | FL | 850-469-7040 | | |
| Baptist Physician | CT | | | | |

Records 1 to 15 of 339    Next    Last

New Search I Print Version

*FIG. 3x*

| Referral Dashboard | Lab Dashboard | Create Referral | Search Referrals |   Welcome Back Specialist Demo Main Desk | Logout Markets    Groups & Doctors    Office Staff    Insurance Providers Baptist Hospital (Pensacola)
Address:         1717 North E. Street
                 Pensacola, FL  32501
Phone 1:         850-469-7040
Phone 2:
Fax:
Email:           outpatientscheduling@bhcpns.org
Website:         http://www.bhcpns.org/Home/
Vision Enabled:  False
Market:

Doctors
Radiology/Diagnostic Imaging    Baptist Physician
Speech & Hearing Therapy        Baptist Physician
Ultrasound                      Baptist Physician
Nuc Medicine                    Baptist Physician
MRI                             Baptist Physician
Mammography                     Baptist Physician
Dexascan                        Baptist Physician
CT                              Baptist Physician ← Back

FIG. 3y

| Referral Dashboard | Lab Dashboard | Create Referral | Search Referrals | Welcome Back Main Desk Primary Demo | Logout |

Group Management

| UID | Permission | Name | Phone | Logins | Login Failures | Active |
|-----|------------|------|-------|--------|----------------|--------|
| 117 | OFFICE | Nicholson, Keith | 850-434-8307 | 0 | 0 | False |
| 116 | GROUP | Wirth, James | 850-438-0394 | 3 | 0 | False |
| 118 | ADMIN | White, Jamie | 850-434-8007 | 114 | 0 | True |
| 70  | GROUP | Main Desk, Primary Demo | 850-434-8007 | 2777 | 0 | True |
| 221 | OFFICE | Account, Test | 850-434-8007 | 7 | 2 | False |

Insert

| GroupID | Name | Phone 1 | Phone 2 | Fax | Email | Active |
|---------|------|---------|---------|-----|-------|--------|
| Edit | Update Insurance Preferences | | | | | |
| | Plugit-Primary Care | 850-434-8007 | | | white@plugit.com | True |

| Referral Dashboard | Lab Dashboard | Create Referral | Search Referrals | Welcome Back Main Desk Primary Demo | Logout |

Edit User
- Uid: 116
- First Name*: James
- Last Name*: Wirth
- Phone*: 850-438-0394
- Fax:
- City: Pensacola Access Control
- Email: james@plugit.com
- Login: wirth
- Active: ☐
- Group: ☑ Plugit-Primary Care
- Doctors: Plugit-Primary Care
  - ☑ Nicholson, Keith
  - ☑ Wirth, James

[Update Record]

*Required Field

*FIG. 3aa*

| Referral Dashboard | Lab Dashboard | Create Referral | Search Referrals | Welcome Back Main Desk Primary Demo I Logout |

Group Management

| UID | Permission | Name | Phone | Logins | Login Failures | Active |
|---|---|---|---|---|---|---|
| 117 | OFFICE | Nicholson, Keith | 850-434-8307 | 0 | 0 | False |
| 116 | GROUP | Wirth, James | 850-438-0394 | 3 | 0 | False |
| 118 | ADMIN | White, Jamie | 850-434-8007 | 114 | 0 | True |
| 70 | GROUP | Main Desk, Primary Demo | 850-434-8007 | 2777 | 0 | True |
| 221 | OFFICE | Account, Test | 850-434-8007 | 7 | 2 | False |

Insert

| GroupID | Name | Phone 1 | Phone 2 | Fax | Email | Active |
|---|---|---|---|---|---|---|
| Edit I Update Insurance Preferences | | | | | | |
| | Plugit-Primary Care | 850-434-8007 | | | white@plugit.com | True |

FIG. 3bb

| Referral Dashboard | Lab Dashboard | Create Lab Request | Search Lab Request | Welcome Back Main Desk Primary Demo I Logout |

Lab Request Aging Report
Less than 30 days old

| Patient | To | From | Status Date/Age | ✉ |
|---|---|---|---|---|
| Doe, John | Baptist Hospital Lab | Plugit-Primary Care | 4/17/2003 11:17:39 AM | 0/0 |
| Bushler, Jeremy | Baptist Hospital Lab | Plugit-Primary Care | 4/29/2003 9:44:32 AM | 0/0 |
| Bushler, Jeremy | Baptist Hospital Lab | Plugit-Primary Care | 5/7/2003 10:14:54 AM | 0/0 |

31-60 days old

| Patient | To | From | Status Date/Age | ✉ |
|---|---|---|---|---|
| Doe, John | Baptist Hospital Lab | Plugit-Primary Care | 4/11/2003 7:42:13 AM | 0/0 |

* Click on Patient Name for Full Details

FIG. 3cc

| Referral Dashboard | Lab Dashboard | Create Lab Request | Search Lab Request | Welcome Back Main Desk Primary Demo | Logout |

| 1. Start | 2. Patient | 3. Select Lab | 4. Select Tests | 5. Preview and Send | Start New Lab Request |

1. Start

Social Security Number*: [          ]
Ex. 555-55-5555 or 555555555

Priority: [Normal ▽]

Referral Authorization Number: [                    ]

Authorization Expires: [    ] / [    ] / [    ]
mm/dd/yyyy ex: 01/05/2003

Standing: [    ]

Standing Expiration: [    ] / [    ] / [    ]
mm/dd/yyyy ex: 01/05/2003

[Next →]

*Required Field

| Referral Dashboard | Lab Dashboard | Create Lab Request | Search Lab Request | Welcome Back Main Desk Primary Demo | Logout |

| 1. Start | 2. Patient | 3. Select Lab | 4. Select Tests | 5. Preview and Send | Start New Lab Request |

Current Favorites:
Test Number      Test Name      🗑 Remove from Favorites

[Continue →]

Search for Lab Tests
Enter Keyword: [                              ]    [Search]
A B C D E F G H I J K L M N O P Q R S T U V W X Y Z

Search Results
Test Number      Test Name      Add to Favorites
[Add]

FIG. 3gg

| Referral Dashboard | Lab Dashboard | Create Lab Request | Search Lab Request | Welcome Back Main Desk Primary Demo | Logout |

1. Start  2. Patient  3. Select Lab  4. Select Tests  5. Preview and Send     Start New Lab Request

2. Patient

SSN 555-55-5555
First Name*: John
Last Name*: Doe
Address 1: 2211 Biasden
Address 2:
City: Pensacola
State: FL
Zip: 32503
Home Phone*: 888-888-8888
Work Phone*: 999-999-9999

Physical

DOB*: 07 / 04 / 1970
mm/dd/yyyy
Height: 5'11"
Weight: 170

Insurance

Primary*: BC/BS of Florida
Number: XJG55555555555
Group: 123457
Secondary Insurance: Beech Street
Number: eeeeeee
Group: eeeeeee
Insurance Reviewed: ☐ *

Next →
*Required Field

*FIG. 3ee*

| Referral Dashboard | Lab Dashboard | Create Lab Request | Search Lab Request | Welcome Back Main Desk Primary Demo | Logout 1. Start   2. Patient   [3. Select Lab]   4. Select Tests   5. Preview and Send     Start New Lab Request 3. Select Office From Doctor*: Plugit – Primary Care – Test Keith Nicholson MD
Plugit – Primary Care – Wirth, James MD Click to select To Lab*: Baptist Hospital Lab
Lab Not Specified
Sacred Heart Hospital Lab
West Florida Hospital Lab Diagnosis Codes*: [ ] , [ ] , [ ] , [ ] , [ ]
Click here for ICD-9 Code Listing
Separate multiple diagnosis codes with a comma Diagnosis Notes/Comments*: [ ]

Doctor Signature Required: [✓]

[Next →]
*Required Field

*FIG. 3ff*

| Referral Dashboard | Lab Dashboard | Create Lab Request | Search Lab Request | Welcome Back Main Desk Primary Demo | Logout 1. Start   2. Patient   3. Select Lab   | 4. Select Tests |   5. Preview and Send          Start New Lab Request

Current Favorites:
Test Number          Test Name          🗑 Remove from Favorites Continue →

Search for Lab Tests
Enter Keyword: [                    ]          [ Search ]
A B C D E F G H I J K L M N O P Q R S T U V W X Y Z

Search Results
Test Number          Test Name          Add to Favorites
85027     BLOOD COUNT; COMPLETE CBC, AUTOMATED          ☐
          (HGB, HCT, RBC, WBC, & PLATELET)
85025     BLOOD COUNT; COMPLETE CBC, AUTOMATED          ☐
          (HGB, HCT, RBC, WBC, & PLATELET) &
          AUTOMATED DIFFERENTIAL WBC
                                                        [ Add ]

*FIG. 3hh*

| Referral Dashboard | Lab Dashboard | Create Lab Request | Search Lab Request | Welcome Back Main Desk Primary Demo | Logout 1. Start   2. Patient   3. Select Lab   | 4. Select Tests |   5. Preview and Send          Start New Lab Request

Current Favorites:
            Test Number          Test Name          🗑 Remove from Favorites
☐    85027     BLOOD COUNT; COMPLETE CBC, AUTOMATED          ☐
               (HGB, HCT, RBC, WBC, & PLATELET)
               AUTOMATED DIFFERENTIAL WBC
☐    85025     BLOOD COUNT; COMPLETE CBC, AUTOMATED          ☐
               (HGB, HCT, RBC, WBC, & PLATELET) &

Continue →

Search for Lab Tests
Enter Keyword: [                    ]          [ Search ]
A B C D E F G H I J K L M N O P Q R S T U V W X Y Z

Search Results
Test Number          Test Name          Add to Favorites
                                                        [ Add ]

*FIG. 3ii*

| Referral Dashboard | Lab Dashboard | Create Lab Request | Search Lab Request | Welcome Back Main Desk Primary Demo | Logout |

1. Start  2. Patient  3. Select Lab  4. Select Tests  | 5. Preview and Send |    Start New Lab Request

```
5. Preview and Send
    Lab Request is ready to be sent!
         Send This Lab Request
```

Lab Request Information
From Group:            Plugit – Primary Care
From Doctor:           Wirth, James MD
Lab:                   Lab Not Specified
Referral Request Number:
Auth. Expire Date:
Priority:              Normal
Lab Tests Requested:
    68360              CONJUNCTIVAL FLAP;
                       BRIDGE PARTIAL (SEP
                       PROC)
    42145              PALATOPHARYNGOPLASTY Originator:            Main Desk, Primary Demo
Created:               5/14/2003

Diagnosis
Diagnosis Codes:   677...
Diagnosis Notes:   NONE

Patient Information
Name:              Doe, John
SSN:               555555555
Address:           2211 Biasden
                   Pensacola, FL 32503
Home Phone:        888-888-8888
Work Phone:        999-999-9999
Date of Birth:     07/04/1970
Height:            5'11"
Weight:            170
Gender:            Male
Primary Insurance: BC/BS of Florida
                   XJG55555555555
                   123456
Secondary Insurance: Beech Street
                     eeeeeee
                     eeeeeee
Signature on File:   False

*FIG. 3jj*

| Referral Dashboard | Lab Dashboard | Create Lab Request | Search Lab Request | Welcome Back Main Desk Primary Demo | Logout Lab Request Lab Request fully sent!

Review this Lab Request | Create a New Lab Request | Home

Click Here to Print Lab Test Request

*FIG. 3kk*

| Referral Dashboard | Lab Dashboard | Create Lab Request | Search Lab Request | Welcome Back Main Desk Primary Demo | Logout Search Lab Referrals
  Patient Name: [            ]
                Partial Names OK
  Patient SSN:  [            ]
                    Submit

*FIG. 3LL*

| Referral Dashboard | Lab Dashboard | Create Lab Request | Search Lab Request | Welcome Back Main Desk Primary Demo | Logout Search Results

| Patient | To | From | Date Sent | Messages |
|---|---|---|---|---|
| Doe, John | Baptist Hospital Lab | Plugit-Primary Care Test Keith Nicholson MD | 5/14/2003 9:34:42 AM | 0/0 |
| Doe, John | Baptist Hospital Lab | Plugit-Primary Care James Wirth MD | 4/17/2003 11:17:39 AM | 0/0 |
| Doe, John | Baptist Hospital Lab | Plugit-Primary Care Test Keith Nicholson MD | 4/11/2003 7:42:13 AM | 0/0 |

*FIG. 3mm*

Shed Procedures

1. Start  2. Patient  3. Select Office  4. Preview and Send          Start New Referral NOTE: Required Field
1. Start Market:               Florida - Pensacola MSA SSN:                  Alabama – Birmingham MSA
Priority:             Alabama – East MSA
Scheduling:           Alabama – Montg. MSA
Referral Auth. No:    Alabama – North MSA
Auth Expires:         Florida – Ft. Walton
Number of Visits:     Florida – Jacksonville
Specialty/Modality:   Florida – Orlando
                      Florida – Panama City
                      Florida – Pensacola MSA
                      Florida – Tampa
                      Florida – Lakeland
                      .
                      .

Select any market in the system and change markets

*FIG. 12b*

METHOD AND SYSTEM FOR ONLINE SECURE PATIENT REFERRAL SYSTEM

CROSS REFERENCE TO RELATED APPLICATION

This application is a continuation of U.S. patent application Ser. No. 11/152,724 filed Jun. 14, 2005, now U.S. Pat. No. 7,702,524, which is a continuation-in-part of U.S. patent application Ser. No. 10/869,809, filed Jun. 16, 2004, which claims priority to U.S. Provisional Application Ser. No. 60/478,933 filed Jun. 16, 2003, each of which is incorporated herein by reference in its entirety.

COPYRIGHT NOTICE

A portion of the disclosure of this patent document, including Figures, contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD OF THE INVENTION

The present invention relates to a secure, web-based, HIPAA compliant, patient file transfer system. Specifically, the invention relates to a system and method for allowing physician offices to order outpatient tests and procedures electronically and transfer patient files and insurance information to recipients (e.g., other doctors, hospitals, etc.) on the system.

BACKGROUND OF THE INVENTION

One of the more significant developments in the computing industry in the last few years has been the emergence of the World Wide Web (WWW). With the Web, a computer operator, equipped with an appropriately connected computer and a software package called a browser, can explore vast amounts of information stored on computers around the world. Navigating (surfing) the Web is relatively simple, typically requiring only clicking a computer mouse to move between Web documents, even when the documents are located at separate locations.

HTML (HyperText Markup Language) is a language used to provide information on the Web. HTML provides a rich lexicon and syntax for designing and creating useful hypertext and hypermedia documents. With HTML, Web designers can describe the format and content of a Web document, which may include, for example, text filed, graphics files, and multimedia files. When accessed by a client computer (i.e., the computer local to the browser), the HTML file is transmitted to the client computer over a network such as the Internet and interpreted by the browser. Other protocols and standards exist for interacting with computers on the Internet/Intranet, including .ASP for a dynamically created Web page that utilizes ActiveX scripting—usually VB Script or Jscript code. When a browser requests an ASP, the Web server generates a page with HTML code and sends it back to the browser. In addition, instead of interacting with an application or a single Web site, .NET can connect the user to an array of computers and services that will exchange and combine objects and data.

Due to the new HIPAA legislation, medical practices (offices and hospitals) need a secure manner to transfer patient information to other medical facilities quickly and confidentially. Current practice is to use the telephone, fax, mail and courier. Problems associated with sending patient information to offices and medical facilities using the fax machine include the chance of sending the information to the wrong fax number, fax being illegible, not all the pages being transmitted, incomplete data, offices losing the faxes that do come through, and no "mirrored" record of delivery and receipt of the information. Problems associated with trying to schedule appointments and transferring information via the phone include no audit trail, playing phone tag and waiting on hold.

Therefore, there is a need in the art for a method by which patient files and orders can be transferred with minimized phone calls and faxes between physician offices and local hospitals, labs, and the like. There is also a need in the art for the secure transmission of patient files and orders, allowing for an audit trail that shows who, when and where opened, reviewed or acted on a file.

BRIEF SUMMARY OF THE INVENTION

The present invention solves the above-stated problems in the art by providing a system and method for allowing medical offices and hospital staff to transfer patient information and files securely and confidentially within and between medical offices. By using a combination of security protocols the system converts the existing Internet into a secure information transportation medium and channel that meets HIPAA requirements for transferring patient information.

Features of the invention can be implemented in numerous ways, including as a system, a method, a computer site, or a computer readable medium. The invention preferably relies on a communications infrastructure, for example the Internet, wherein individual interaction is possible. Several embodiments of the invention are discussed below.

As a computer system, part of the invention generally includes a database and a processor unit. The processor unit operates to receive information (patient files) and to analyze the received information to generate an electronic file. The output may include print or electronic media. Part or all of the data can also be sent electronically and maintained on a web server for confidential access with typical browsers. The data may also be transmitted and viewed by other well known techniques such as email, interactive television, and the like. The computer site is preferably viewed with a client web browser as an HTML document through a web secure server communicating with an application server having a database associated therewith. The present invention is not limited to any particular platform for network (Internet, Intranet) communication and other platforms, including .ASP and .NET, etc. are contemplated herein. The system may be an Internet or other broadband computer-based networked system. The system includes an encrypted collection of electronic patient records of a plurality of persons wherein: the patient records are obtained and electronically compiled and are transmissible in whole or in part for referral purposes and for outpatient service orders. The patient records include patient demographic information, patient insurance information, patient charts, physician notes, patient test results, patient lab tests. The information for file ordering/file transfer (referrals) is transferred through a novel process for security including Start Screen, Patient Screen, Physician/Doctor Screen, and Preview/Send Screen. The patient records/file is also tagged with status information. Time stamping is provided. Summary pages are provided as a "dashboard". Fields are defined in the system to ensure complete transmission of critical data (including but not limited to): Patient SSN, referral authorization number, specialty, patient name, patient telephone number, primary insurance, physician signature on file, insurance information reviewed, from physician, to physician, diagnosis codes.

The invention includes a network server comprising a processor and memory wherein the memory includes a plurality of patient records associated with respective patients, each record having certain specifically defined fields of information to ensure transfer of complete records during referral or lab orders.

As a method, the invention includes steps for patient referral and lab order entry. These steps utilize specific information gathering to ensure security. The method includes obtaining and compiling a patient record pertaining to a patient; electronically inputting the patient record obtained into a secure computer database containing other patient records, allowing physician access to the patient record wherein the access includes allowing the physician to make lab orders and send part of the patient information, including certain defined fields for a complete record and to send and receive referrals including certain defined fields for a complete record.

As a computer site, the invention includes windows and code devices for patient referral and lab order entry. The data entry screens are designed to be user friendly but also capture the requisite information for secure processing. Unique "dashboards" are provided for each user using the system.

As a computer readable medium containing program instructions for collecting, analyzing and generating output, an embodiment of the invention includes computer readable code devices for interacting with a user as noted above, processing that data, and generating printed or electronic media for that user.

In a specific embodiment, the invention provides a method for secure transfer of patient information from a sender to a recipient, including: (a) receiving from sender initial data regarding a patient including a predetermined set of initial data fields; (b) receiving from sender patient specific data including a predetermined set of patient specific data fields; (c) receiving from sender recipient data including a predetermined set of recipient fields; and (d) displaying said initial data, patient specific data, and recipient data for sender review; and (e) sending patient information to recipient. The predetermined set of initial data fields may include patient social security number, priority, scheduling options, referral authorization information number. The predetermined set of patient specific data fields may include last name, first name, date of birth, gender, primary insurance and phone. The predetermined set of recipient data fields may include sender, recipient, diagnosis codes, diagnosis notes. The method also includes storing patient specific data for later auto insertion by sender and by recipient. The method further includes storing of an audit trial associated with each transfer comprising date and time stamping every user access. By completing the predetermined set of data fields, a complete order or referral can be accomplished without the need for collection of further information.

A status monitor for the transfer is also automatically updated which displays current status of the transfer and authorized actions available for sender and recipient for the current status. The status monitor is displayed to both the sender and recipient. The status monitor is preferably displayed via a user interface having an interactive display program for displaying current status of the transfer and authorized actions available for sender and recipient for the current status.

The advantages of the invention are numerous. First and foremost, the invention provides for a method by which physicians can order lab tests and transfer patient files and insurance information over a secure, web-based system. A resulting advantage is the ability to convert the existing Internet infrastructure, using a combination of security protocols, into a secure medical information transportation medium and channel that meets HIPAA requirements for transferring patient information.

Other aspects and advantages of the invention will become apparent from the following detailed description taken in conjunction with the accompanying drawings, illustrating by way of example the principles of the invention.

All patents, patent applications, provisional applications, and publications referred to or cited herein, or from which a claim for benefit of priority has been made, are incorporated herein by reference in their entirety to the extent they are not inconsistent with the explicit teachings of this specification. The following patents are incorporated by reference: U.S. Pat. No. 6,263,330, U.S. Patent Application No. 2002/0016923, U.S. Patent Application No. 2003/0050803.

BRIEF DESCRIPTION OF THE DRAWINGS

The present invention together with the above and other objects and advantages may best be understood from the following detailed description of the preferred embodiments of the invention illustrated in the drawings, wherein:

FIGS. 12a and 12b show example screen displays for geographic markets.

Figure 1A:
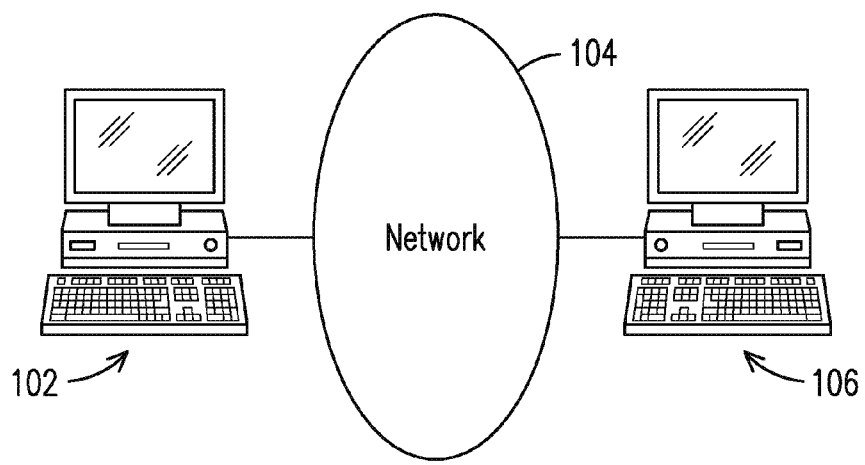
FIG. 1a is a high level diagram of an exemplary computing system network on which the present invention may be implemented.

It should be understood that in certain situations for reasons of computational efficiency or ease of maintenance, the ordering of the blocks of the illustrated flow charts could be rearranged or moved inside or outside of the illustrated loops by one skilled in the art. While the present invention will be described with reference to the details of the embodiments of the invention shown in the drawing, these details are not intended to limit the scope of the invention.

DETAILED DISCLOSURE OF THE INVENTION

Reference will now be made in detail to the embodiments consistent with the invention, examples of which are illustrated in the accompanying drawings. Wherever possible, the same reference numerals used throughout the drawings refer to the same or like parts.

The present invention solves the problems in the art by providing a system and method for allowing medical offices and hospital staff to transfer patient information and files securely and confidentially within and between medical offices. Preferably, the invention is operated in conjunction with an interactive web site.

The present invention generally comprises a client web interface (CWI) application for graphical user interface (GUI), maintenance (back-end) applications to support the Site, database server software and the database associated therewith, and an administrative interface, each of which will be discussed in detail below.

FIG. 1a is a high level diagram of an exemplary computing system network on which the present invention may be implemented. The system includes a web server 102 for storing web pages, and a client computer 106 capable of accessing the web pages on server 102. Server 102 may be any number of known computers, or network of computers, capable of hosting a website. Similarly, client 106 may be any number of known computers, or network of computers, capable of supporting a web browser. Server 102 and client 106 are coupled to one another via a network 104, such as the Internet. To retrieve a web page stored on server 102, the user of client 106 specifies a URL (uniform resource locator). The specified URL allows web-browsing software running on client 106 to initiate communication with server 102 and access the desired HTML page, which a browser interprets and displays on client 106.

Figure 1B:
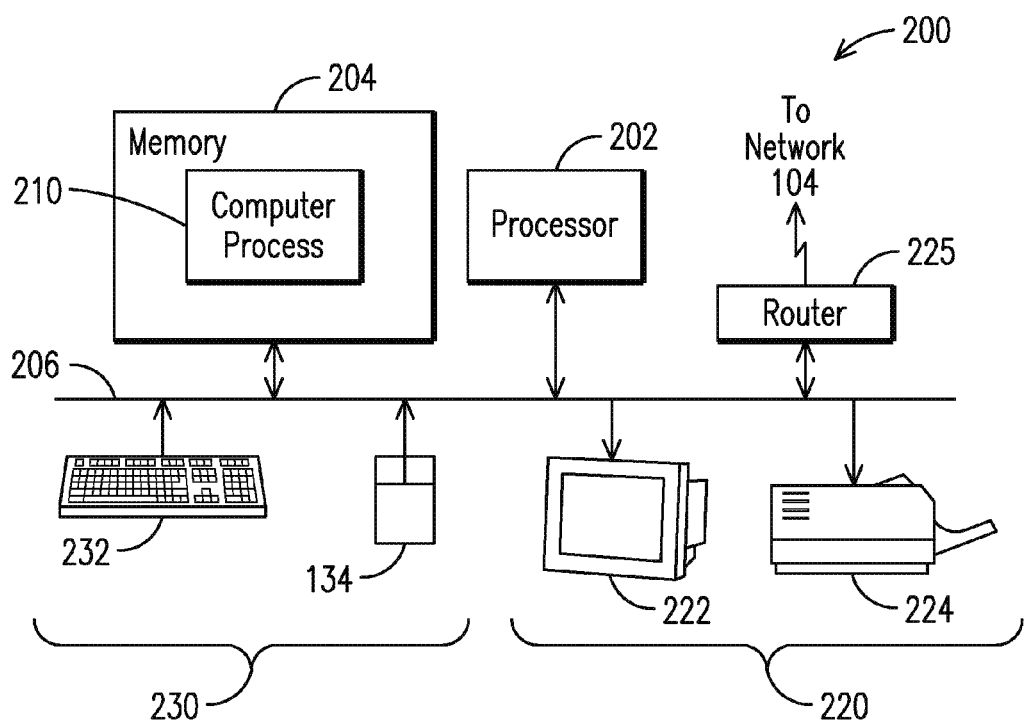
FIG. 1b is a more detailed diagram of an exemplary system.

FIG. 1b is a more detailed diagram of a computer system 200, which may be client 106 or server 102. The computer system 200 includes a processor 202 and a memory 204 coupled to the processor 202 through a bus 206. The processor 202 retrieves computer instructions from memory 204 and executes those instructions. The processor 202 also (1) reads data from and writes data to memory 204, (2) sends data and control signals through bus 206 to one or more computer output devices 220, (3) receives data and control signals through bus 206 from one or more computer input devices 230 in accordance with the computer instructions, and (4) transmits and receives data through bus 206 and router 225 to network 104.

Memory 204 can include any type of computer memory including, without limitation, random access memory (RAM), read-only memory (ROM), and storage devices that include storage media such as magnetic and/or optical disks. Memory 204 includes a computer process 210, such as web browser or web server software. A computer process includes a collection of computer instructions and data that collectively defines a task performed by the computer system 200.

Computer output devices 220 can include any type of computer output device, such as a printer 224, a cathode ray tube (CRT) 222 (alternatively called a monitor or display), a light-emitting diode (LED) display, or a liquid crystal display (LCD). CRT display 222 preferably displays the graphical and textual information of the web browser. Each of the computer output devices 220 receives from the processor 202 control signals and data and, in response to such control signals, displays the received data.

User input devices 230 can include any type of user input device such as a keyboard 232, or keypad, or a pointing device, such as an electronic mouse 234, a trackball, a light-pen, a touch-sensitive pad, a digitizing tablet, thumb wheels, or a joystick. Each of the user input devices 230 generates signals in response to physical manipulation by a user and transmits those signals through the bus 206 to the processor 202.

As previously discussed, to view a web page on client 106, the user specifies, via a URL, the location of the desired web page. The browser on client 106 then retrieves the HTML file for the specified web page, interprets the file, and displays it as a web page.

Figure 2:
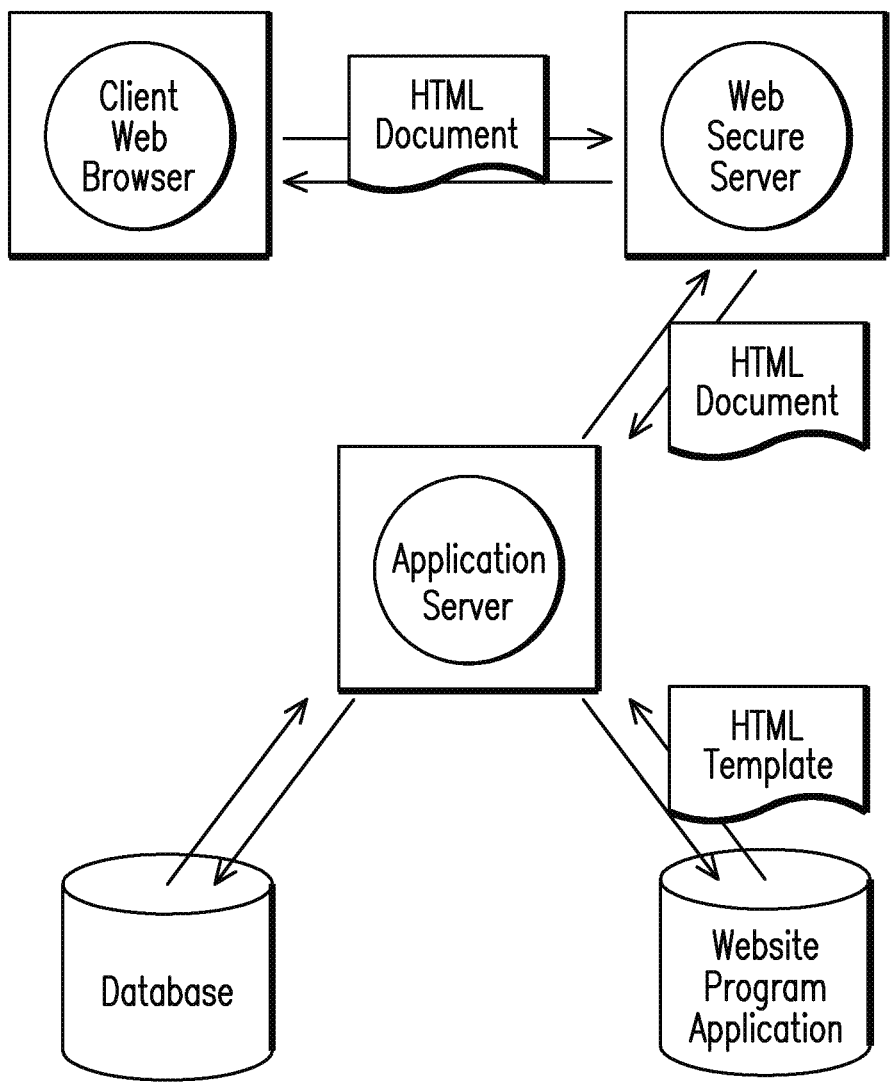
FIG. 2 is an overview of a simplified embodiment of hardware architecture for implementation of the present invention as client/server architecture for HTML documents.

FIG. 2 is an overview of a simplified embodiment of hardware architecture for implementation of the present invention as client/server architecture for HTML documents. The architecture preferably comprises at least two networked computer processors (client component and server component(s)) and a database(s). The computer processors can be processors that are typically found in personal desktop computers (e.g., IBM, Dell, Macintosh), portable computers, mainframes, mini-computers, Unix systems, or other computing devices. Preferably in the networked client/server architecture of the present invention, a classic two or three tier client/server model is utilized. Preferably, a relational database management system (RDMS), either as part of the Application Server component or as a separate component (RDB machine), provides the interface to the database.

In preferred database-centric client/server architecture, the client application generally requests data and data-related services from the application server, which makes requests to the database (or the database server). The server(s) (e.g., either as part of the application server machine or a separate RDB/relational database machine) responds to the client's requests and provides access to data. Basic interaction between a client and server is known in the art. In a preferred embodiment of the present invention, a user at a client computer submits a request to the server for a specified action (e.g., modify preferences for custom page). The server receives the request and passes it on to a software program, preferably a CGI (Common Gateway Interface) program that resides in the server computer and processes data submitted from a client. The CGI program processes the data related to the request and dynamically generates a new HTML document and returns it to the server. The server sends the new HTML document to the client. The client then displays the HTML document for the user by using a browser program such as Netscape Navigator. Other requests may be processed or the process may terminate.

More specifically, the client components are preferably complete, stand-alone, personal computers offering a full range of power and features to run applications. The client component preferably operates under any operating system and includes communication means, input means, storage means, and display means. The user enters input commands into the computer processor through input means, which could comprise a keyboard, mouse, or both. Alternatively, the input means could comprise any device used to transfer information or commands. The display comprises a computer monitor, television, LCD, LED, or any other means to convey information to the user. In a preferred embodiment, the user interface is a graphical user interface (GUI) written for web browser applications.

The server component(s) can be a personal computer, a minicomputer, or a mainframe and offer data management (information sharing between clients), network administration, and security. The Database Server (RDBMS—Relational Database Management System) and the Application Server may be the same machine or different hosts if desired.

The present invention also envisions other computing arrangements for the client and server(s), including processing on a single machine such as a mainframe, a collection of machines, or other suitable means. The client and server machines work together to accomplish the processing of the present invention.

The database is preferably connected to the database server component and can be any device that will hold data. For example, the database can consist of any type of magnetic or optical storing device for a computer (e.g., CDROM, internal hard drive, tape drive). The database can be located remote to the server component (with access via modem or leased line) or locally to the server component.

In a preferred embodiment, the present invention operates similar to standard e-commerce sites with the exception of having the additional unique features of the invention. Preferably, the invention is operated as an interactive website with a home page and multiple sub-pages linked thereto to provide the different features of the invention. The typical operation of the website from a user's point of view will now be explained in detail with reference to the appendix, incorporated herein by reference.

Figure 3A:
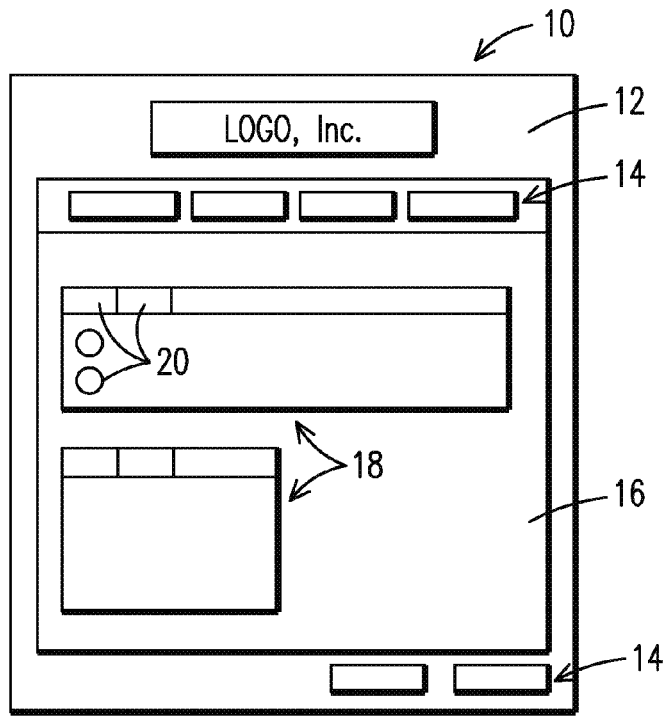
FIG. 3a is an example display screen for the present invention.

An example of a preferred web-based display screen that incorporates features of the present invention is illustrated in FIG. 3a. The display comprises an HTML web page 10, which presents a predetermined layout of resources and information that are available to the user. The method may include other forms of information display, interaction and transfer, including but not limited to .asp and .net. The page may include a suitable banner 12 containing a corporate logo or the like, and one or more navigation buttons, links, hyperlinks, 14 that permit the user to access specific pages associated therewith, e.g. the referral dashboard page, lab dashboard page. Below the banner 12, the current page 16 is displayed. Each page 16 provides the user with a particular type of resource. As will be apparent from the discussion that follows, these resources can be news, informational content, interactive pages/screens, query boxes, data entry, and the like. By interacting with any one of these pages, the user can access the information or services provided. In the example of FIG. 3a, the page 16 includes modules 18 arranged therein. The modules 18 include data and resources for the current page 16. Each module may further include module navigation buttons or links 20 that permit the user to access further modules, data, or pages associated therewith.

Initially, information is collected via a start screen, where the patient's social security number is entered for identification. Subsequent patient screen and physician screen include data such as patient demographic information, patient insurance information, patient charts, physician notes, patient test results and patient lab results.

This data is input into the system manually or directly from the screening devices. This data is analyzed in conjunction with a variety of mechanisms in order to complete a total security system. The system may utilize various algorithms, real-time learning and inference technology, profiling, pattern recognition learning algorithms, neural networks, and the like in order to meet HIPAA requirements for transferring patient information over a secure medium and channel, intended for transporting medical information.

Figure 3B:
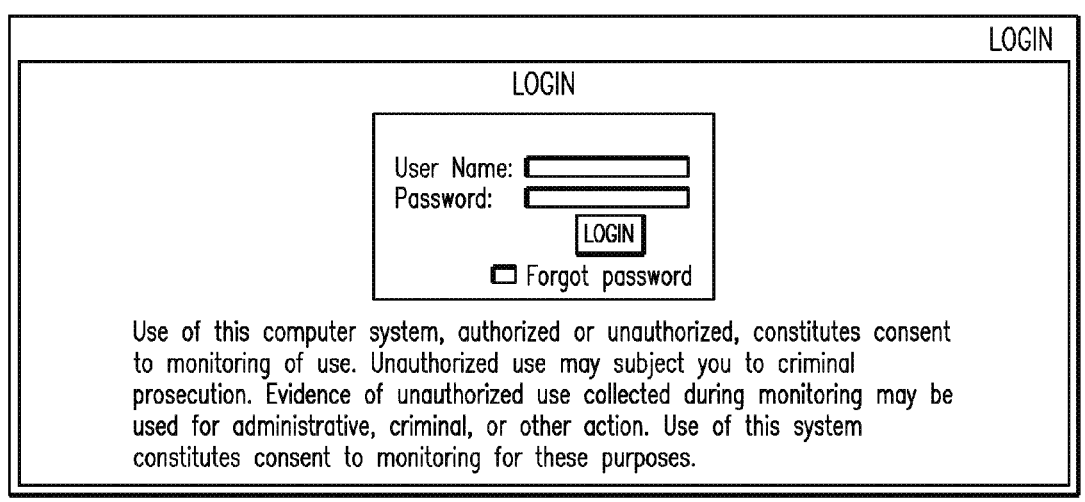
FIGS. 3b-3nn are sample display screens demonstrating use of the invention.
Figure 4:
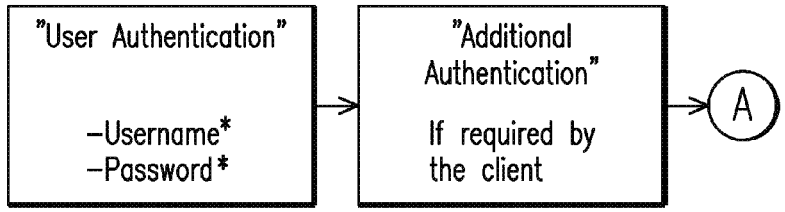
FIG. 4 is a block/flow diagram of the authentication process for Order/File Transfer/Referral section.

Turning now to FIG. 4, to begin utilizing the system (logon), the user is authenticated using standard authentication techniques such as username and password. Additional authentication may also be included if required or requested by the client. An example screen shot of this login process is shown in FIG. 3b.

Figure 5:
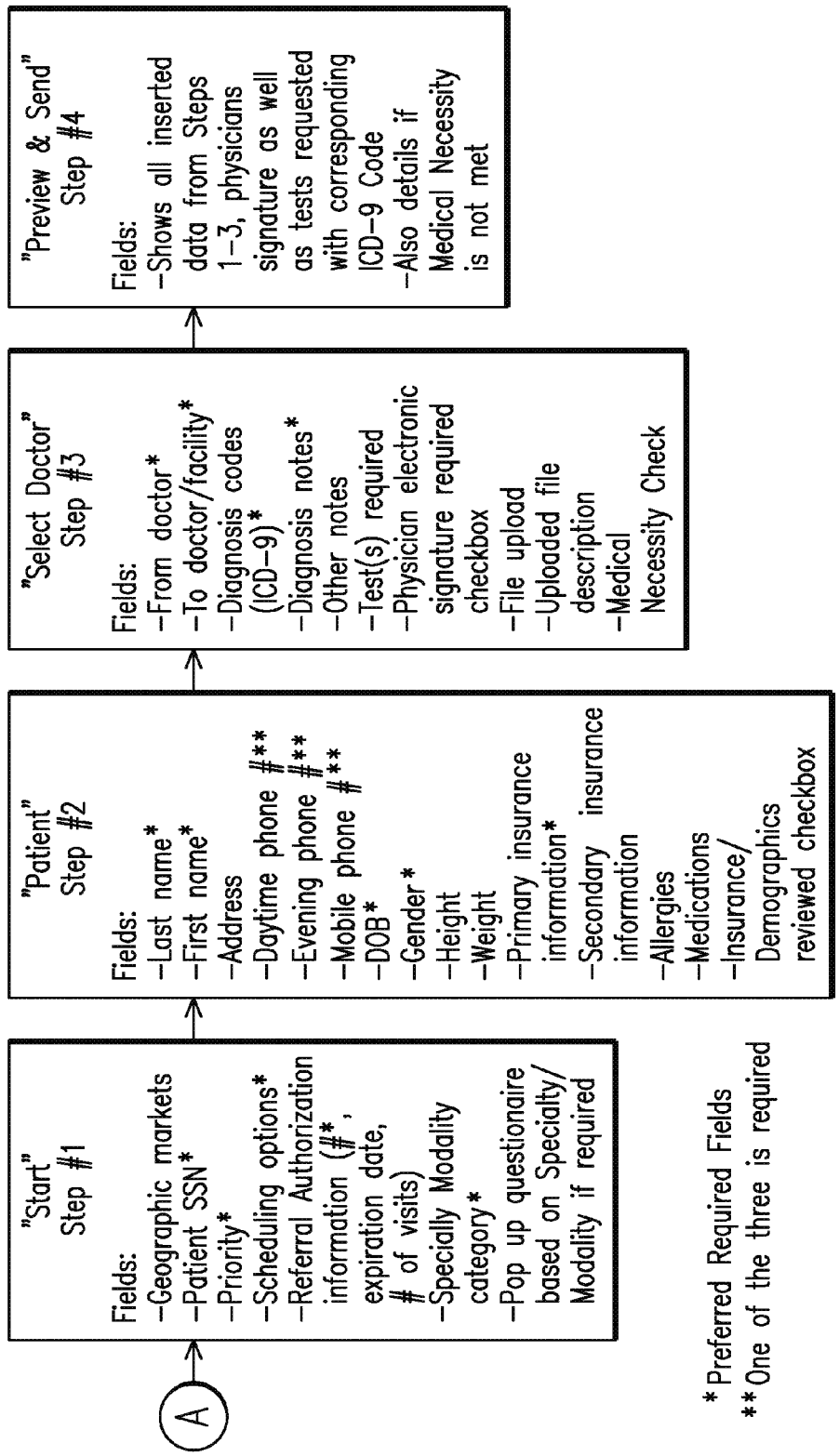
FIG. 5 is a block/flow diagram of the Order/File Transfer/Referral Wizard.

In an embodiment shown in FIG. 5, the system uses a novel 4-step process for transferring patient information, including the following: (1) Start screen requiring a certain number of data entries for security such as: patient social security number, referral authorization and specialty; (2) Patient screen with basic patient demographic information requiring a certain number of data entries for security; (3) Physician screen allowing for communication to and from the doctor in the form of, for instance, diagnosis codes and physician notes and uploads (images, charts and documents), requiring a certain number of data entries for security; and (4); Preview/Send screen, where all information can be reviewed prior to sending. The above-noted steps may be combined into fewer steps or separated into more steps to accomplish the method of the invention without departing from its scope. This process includes any outpatient service where there is a transfer from a physician office to a recipient including but not limited to bed requests, pre-admissions information, etc.).

In a preferred embodiment, the fields for step (1) include geographic market, patient social security number, priority, scheduling option, referral authorization (#, expiration date, # of visits), specialty/modality category, and pop-up questionnaire based on specialty/modality category, wherein in a preferred embodiment the following fields are required for security: patient social security number, priority, scheduling option, referral authorization #, specialty/modality category. See FIG. 3h for an example screen shot of this step.

Figure 3I:
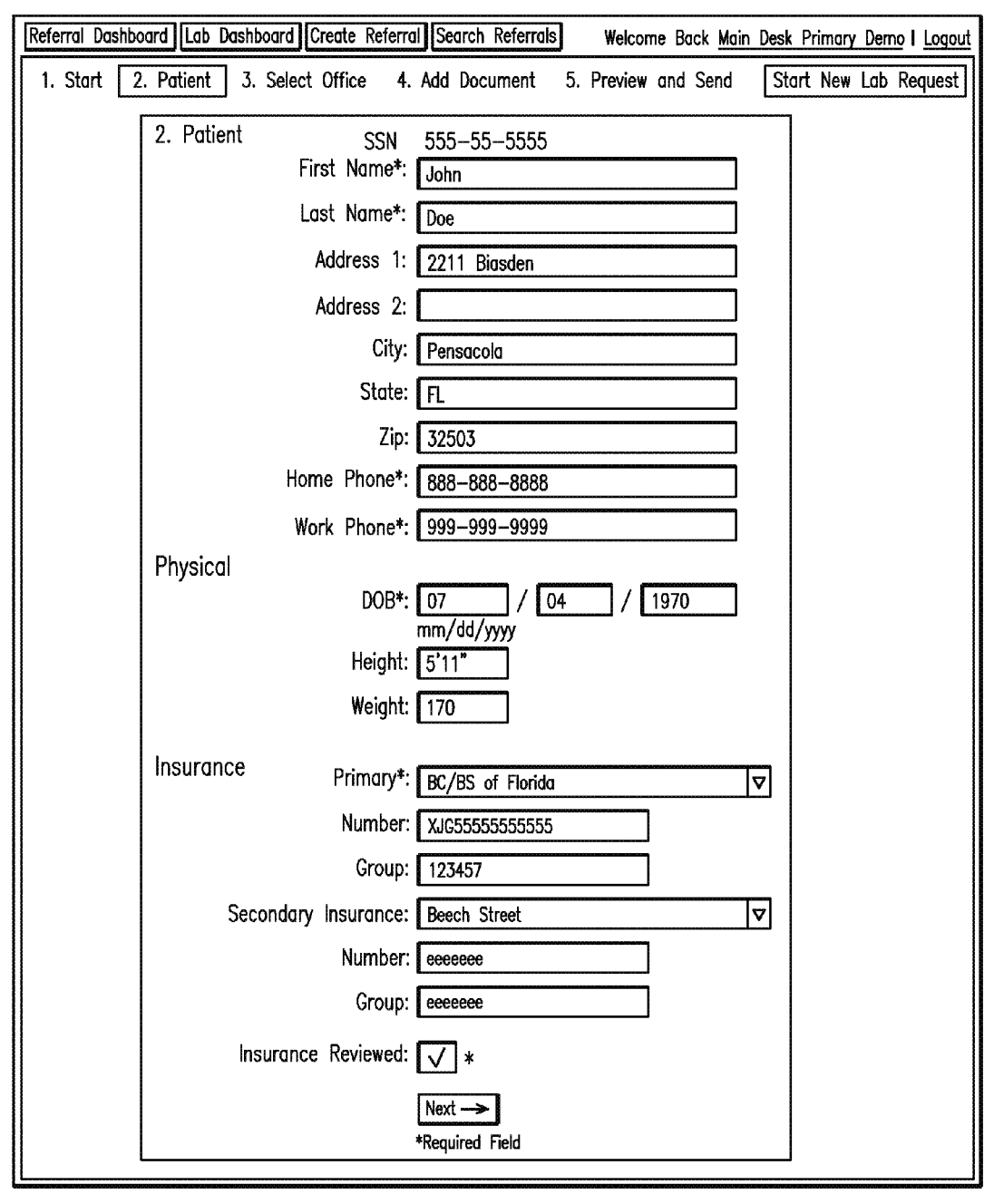

In a preferred embodiment, the data fields for step (2) include last name, first name, address, day phone, evening phone, mobile phone, date of birth, gender, height, weight, primary insurance information, secondary insurance information, allergies, medications, insurance/demographics reviewed checkbox, wherein in a preferred embodiment the following fields are required for security: last name, first name, date of birth, gender, primary insurance, and one of the phone number entries. See FIG. 3i for an example screen shot of this step.

In a preferred embodiment, the data fields for step (3) include from doctor, to doctor/facility, diagnosis codes (ICD-9), diagnosis notes, other notes, test(s) required, physician electronic signature required check box, file upload, uploaded file description, medical necessity check, wherein in a preferred embodiment the following fields are required for security: from doctor, to doctor/facility, diagnosis codes (ICD-9), diagnosis notes. See FIG. 3j-3o for example screen shots of this step (labeled steps 3 and 4a-4e in the figures).

Finally, in a preferred embodiment, the resulting display in step (4) includes a preview of all inserted data from steps 1-3, physicians signature as well as tests requested with corresponding ICD-9 Code and the details of medical necessity if not met. See FIG. 3p for an example screen shot of this step. A confirmation screen may then be provided as shown in FIG. 3q.

After the software of the present invention analyzes the data, the next step in the process is to generate, preferably in real-time when available, an electronic patient file transfer system. The following information can be transferred using one example of the system: (1) Patient demographic information; (2) Patient insurance information; (3) Patient charts; (4) Physician notes; (5) Patient test results; and (6) Patient lab results.

In a preferred embodiment, the system may employ a demographic auto-load. That is, if the patient has ever been loaded into the system previously then patient demographic information can auto-fill based on, for instance, the patient's social security number. This preferred embodiment may limit use of the auto-fill feature to those users who have previously inputted information for the specific patient.

In an embodiment, the system may employ a complete security for file transfer using a variety of mechanisms, of which can include but not limited to the following: (1) System username and password for all system users; (2) Unique username and password; (3) SSL 128 bit encryption for all data transfers; (4) Unique digital certificate for each user; (5) Software firewall; (6) Hardware firewall; (7) Dedicated secure server setup; (8) For active patient file transfers—only the sender and the recipient can see the given patient file transfer specifics and associated documents; (9) For archived patient files—only the sender and the recipient can see the given patient file transfer specifics and associated documents; and (10) Electronic signature for initiating physician.

Figure 7A:
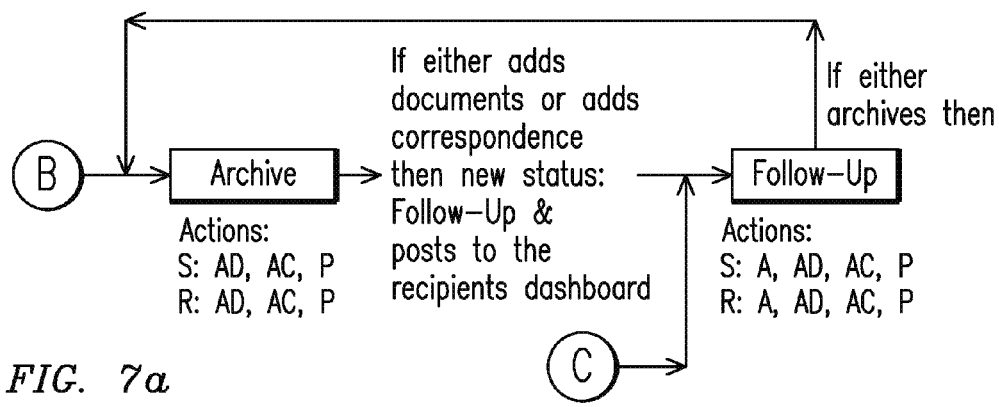
FIGS. 7a and 7b are block/flow diagrams of the authentication process for Order/File Transfer/Referral.
Figure 7B:
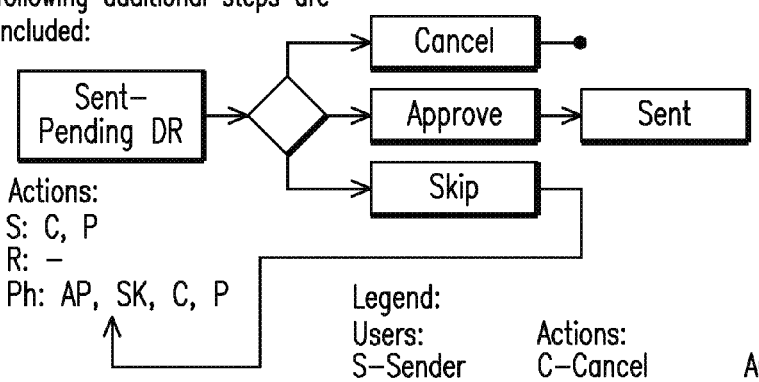
Figure 6:
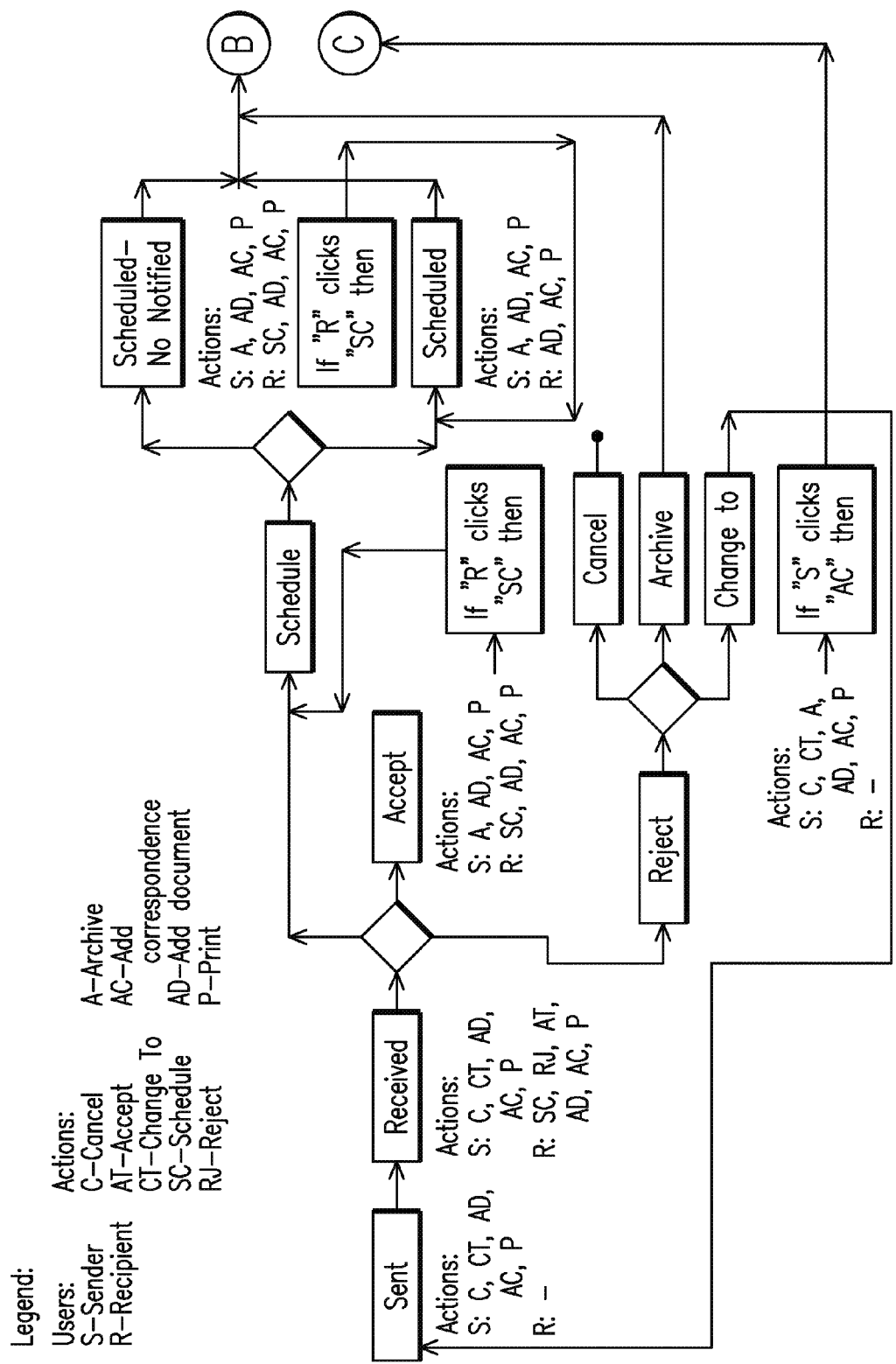
FIG. 6 is a block/flow diagram for Order/File Transfer/Referral section.

The system also includes files status as part of the referral flow as shown in FIGS. 6, 7a, 7b. As the "patient" moves through the system, it is tagged to help the user know the status. An example of statuses are as follows: (1) Sent—the patient file has been sent from the sender to a recipient; (2) Received—the recipient has received the file; (3) Accepted—the recipient has accepted the patient; (4) Rejected—the recipient has rejected the patient (Cancel, Archive, Change to); (5) Scheduled—the recipient has scheduled the patient (Scheduled—not notified and Scheduled); (6) Archived—the patient file transfer has been completed and the file is now in storage; (7) Follow-up. Specifically, after the patient record is received, it then can be (5) Scheduled, (3) Accepted, or (4) Rejected. If Scheduled, then the record is either Scheduled Not Notified or Scheduled. Under Scheduled Not Notified, the recipient can actually click schedule again, which would return the flow to the Schedule option, which allows for user error in regards to scheduling. If rejected, then the record is Cancelled, Archived, or Change to. Cancel ends the record. Archive sends the record to Archive. Change to returns the flow to Sent. Archived referrals can be searched/retrieved by both the sender and recipient. With respect to Follow-up, if either adds documents or adds correspondence, then the Follow-up status posts to the recipients dashboard.

In an embodiment, Removal from the Dashboard occurs as follows: (1) Scheduled—Notified: Sender—auto-archived after 5 days, Recipient—drops from screen 1 day after making referral as "scheduled notified"; (2) Scheduled—Not Notified: Sender—manual archive, Recipient—after sender manually archives the referral; (3) Accepted: Sender—manual archive, Recipient—after sender manually archives the referral or it is auto-archived after 21 days; (4) Rejected: Sender—manual archive, Recipient—immediately after marking referral as rejected.

Additional security measures include alphanumeric password with at least 1 capital character, audit trial—detailed listing of every user who accesses the transaction, time and date stamped, auto-logout after 30 minutes of inactivity, 5 failure lockouts. Number and duration of additional security measures may be modified as appropriate and known in the art.

With respect to transactions, the transactions are unique to the specific sender and the specific recipient and can be searched as any status.

In addition, if physician approval is required by the facility, the following additional steps are included as shown in FIG. 7b: Sent Pending DR then Cancel, or Approve and Sent, or Skip back to Sent-Pending DR.

Figure 8:
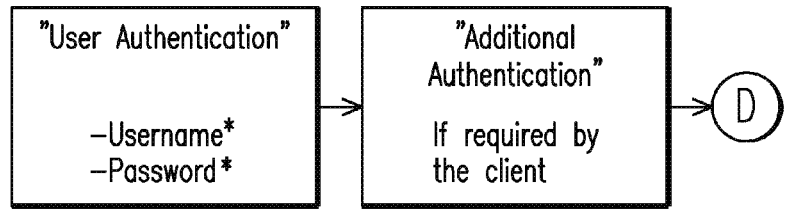
FIG. 8 is a block/flow diagram of the Lab Order Wizard.

Referring now to FIG. 8, the Lab Order process will be described. Initially, the user logs into the system using standard login techniques, e.g., username and password. If additional authentication is required, an additional step may be added.

Figure 9:
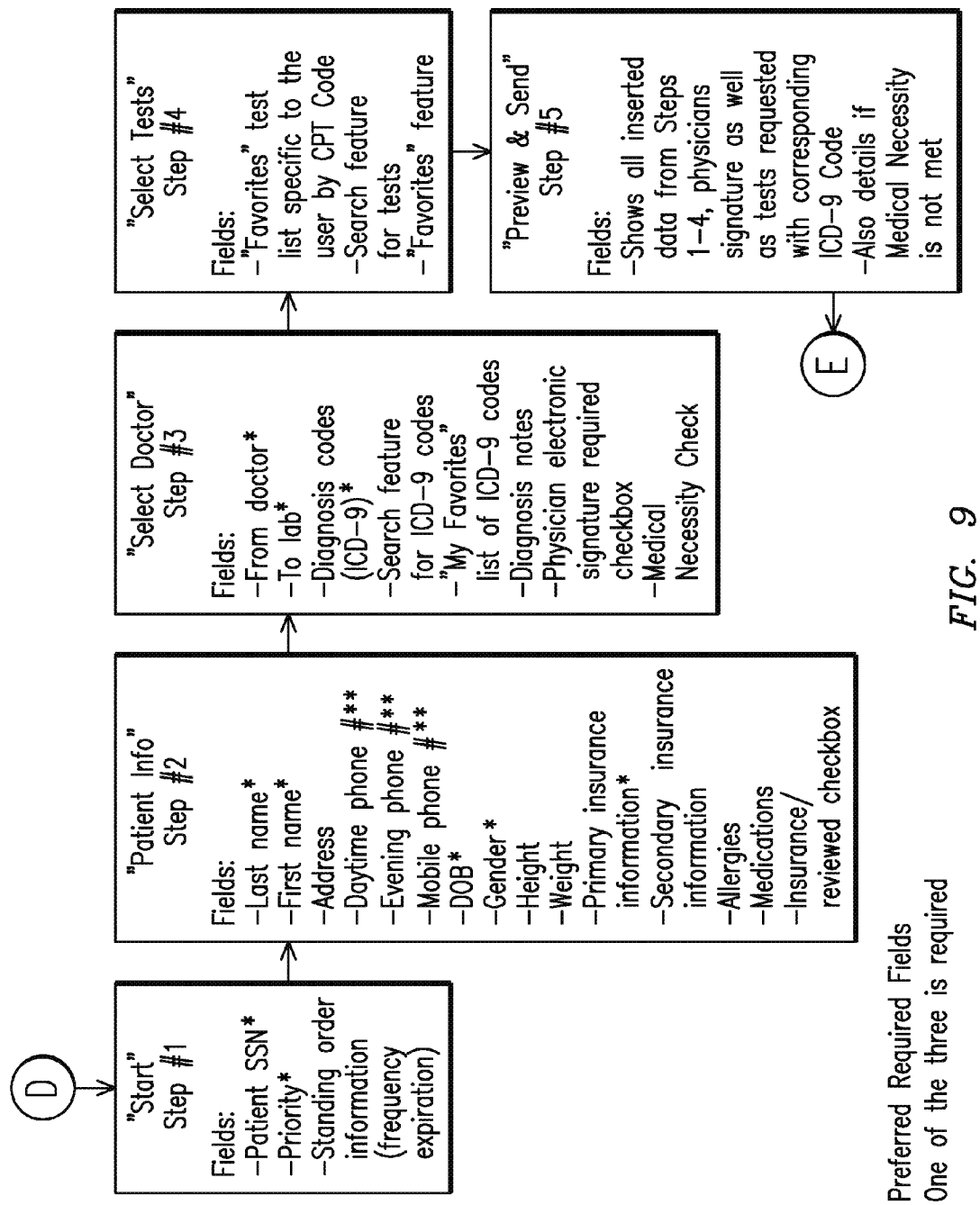
FIG. 9 is a continued block/flow diagram of the Lab Order process.

The Lab Order process utilizes a novel 5 step process as shown in FIG. 9. This process includes the steps of (1) Start, (2) Patient Information, (3) Select Doctor, (4) Select Tests, and (5) Preview and Send. The above-noted steps may be combined into fewer steps or separate into more steps to accomplish the method of the invention without departing from its scope. Moreover, the transfer may be initiated and accomplished with either party being the sender and/or recipient. Preferably the transfers are in real-time.

In a preferred embodiment, the data fields for step (1) include patient social security number, priority, and standing order information (frequency, expiration, wherein in a preferred embodiment the following fields are required for security: patient social security number.

In a preferred embodiment, the data fields for step (2) include first name, last name, address, daytime phone, evening phone, mobile phone, date of birth, height, weight, gender, primary insurance, secondary insurance, allergies, medications, insurance reviewed checkbox, wherein in a preferred embodiment the following fields are required for security: first name, last name, date of birth, gender, primary insurance, and one of the phone numbers.

In a preferred embodiment, the data fields for step (3) include from doctor, to lab, diagnosis codes (ICD-9), search feature for ICD-9 codes, My Favorites list of ICD-9 codes, diagnosis notes, physician electronic signature required checkbox, medical necessity check, wherein in a preferred embodiment the following fields are required for security: from doctor, to lab, diagnosis codes.

In a preferred embodiment, the data for step (4) include "Favorites" test list specific to the user by CPT code, search feature for tests, favorites feature.

In a preferred embodiment, the resulting data in step (5) includes showing all inserted data steps from 1-4, physicians signature as well as tests requested with corresponding ICD-9 code and also details if medical necessity is not met.

Figure 10A:
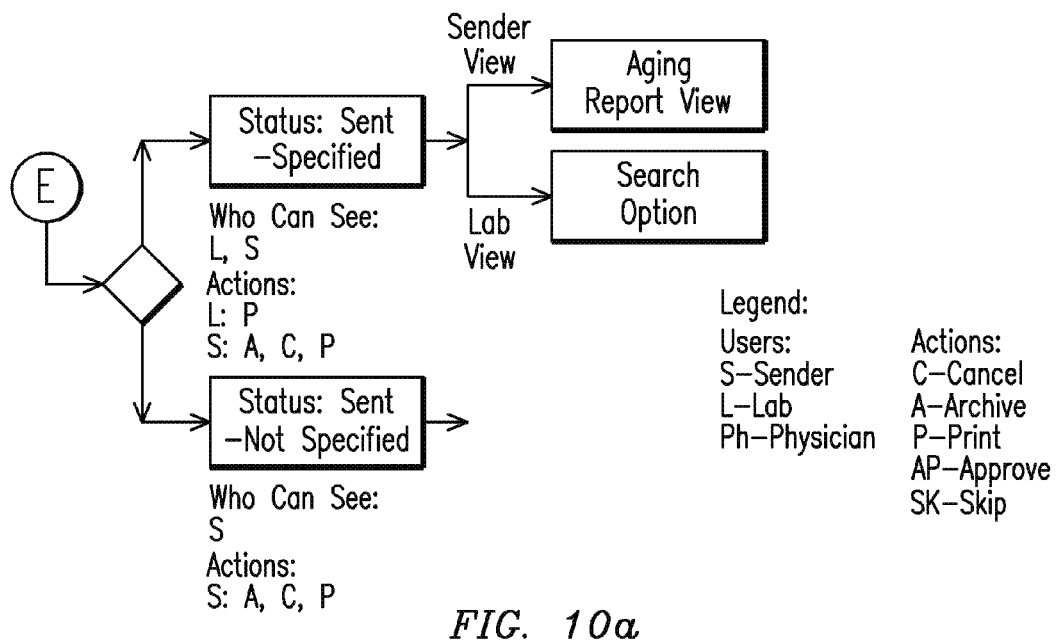
FIGS. 10a and 10b are continued block/flow diagram of the Lab Order process.
Figure 10B:
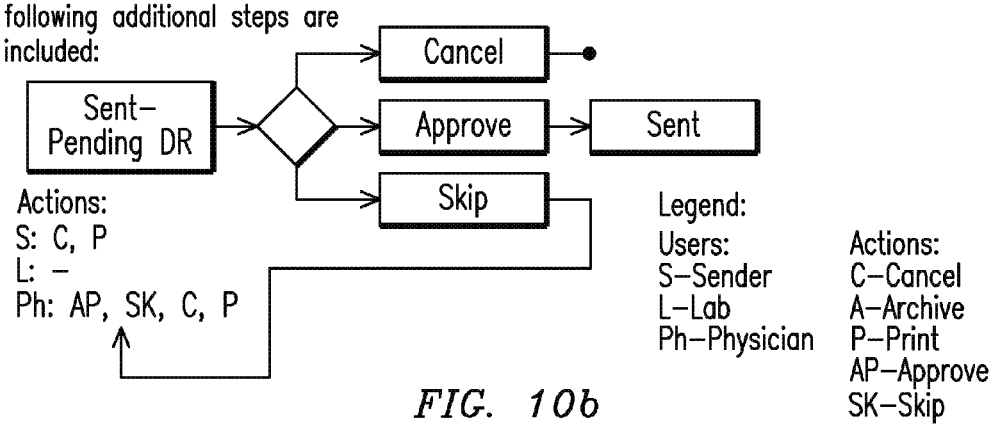

The system also includes files status as part of the lab flow as shown in FIGS. 10a and 10b. As the "patient" lab order record moves through the system, it is tagged to help the user know the status. Examples of statuses are as follows: (1) Sent—Sent Specified or Sent Not Specified. The Sender's view includes an Aging Report View. The Lab's view shows the Search Option. If direct physician approval is required by the facility, the following additional steps are included: Sent Pending DR then Cancel, or Approve and Sent, or Skip back to Sent-Pending DR.

Time stamping is also provided by the system. Time stamping (date and time) of all critical moments in the process of moving the patient file form one location to another (sent, received, accepted/rejected, most recent activity, scheduled, archived, and all correspondence between users/offices) is automatically completed in order to show an audit trail in regards to time and processing.

A Correspondence tool is also provided. The correspondence tool is a secure communication tool that allows users to post messages that only the other office can see (sender or recipient). All communication is encrypted using the security mechanisms of the system. All communication is time stamped (date and time). Appropriate party is notified via an alert on their dashboard with an "attention" icon.

The system has a number of features, including dashboard, priority, audit trial, email notification. A Dashboard is provided. The dashboard is used as the summary page in the system. The dashboard updates in real time and shows the following information: incoming patient files, outgoing patient files, patient name, patient status, from physician, to physician, date of last activity, number of correspondence messages and how many are unread, and priority of patient file transfers. The dashboard can be sorted by: patient name, patient status, from physician, to physician, or date of last activity. The system also provides a priority system. Patient file transfers can be assigned different priorities by the sender. For example, Normal and Stat. Stat is used for patient files that must be processed soon, e.g., within 72 hours. The User audit trial is provided by a system log that logs all users with a time and date stamp whenever the user accesses the file. The system also auto notifies the recipient of a patient file via email whenever a new file is sent.

In order to ensure complete transmission of critical data a pre-defined number of fields may be required to be completed in order to send patient information, for example: Patient SSN, referral authorization number, specialty, patient name, patient telephone number, primary insurance, optional physician signature on file, insurance information reviewed, from physician, to physician, diagnosis codes and notes.

Additional features or modifications to the method of the present invention are available without departing from the scope of the invention. For example, "physician signature on file" may or may not be a required field. System name and password and unique digital certificate may be optional. Terminology for statuses and fields may be modified as the need arises (e.g., changing priority Normal to priority Routine).

Referring now to FIGS. 3b-3nn, the operation of the invention will be explained as an example. The screen shots may vary and may include more or less information than that shown in the example. Multiple screen shots may be combined into fewer screen shots. The order of flow of the screen shots may also vary to implement the methods of the invention.

The program is preferably web based and is launched through a browser, e.g., Internet Explorer. The site address is typed and the system will prompt for a Network user name and password for security. The system's "home page" is then displayed. The Login is next (FIG. 3b). In operation, after logging in, a News page is displayed (FIG. 3c). Buttons on the page include Referral Dashboard and Lab Dashboard. The Referral Dashboard directs the user to the referral dashboard page FIG. 3d which is used for sending patient referrals to other offices, transferring patient files to other offices, and ordering tests (e.g., radiology). The Lab Dashboard directs the user to the lab dashboard section of the system, which allows users to order lab tests at local hospitals and laboratories. The Main Navigation buttons of the system include Referral Dashboard, Lab Dashboard, Create Referral/Create Lab Request, and Search Referral/Search Lab Request.

A unique Referral Dashboard includes incoming referrals and outgoing referrals. It also includes Statuses such as SENT, RECEIVED, REJECTED, SCHEDULED (NOTIFIED), SCHEDULED (NOT NOTIFIED), ACCEPTED, ARCHIVED, and FOLLOW-UP. Other referral actions include CANCEL and CHANGE TO. After clicking the referral status link, the system takes the user to the detailed information page for that referral (FIG. 3e). The following information is listed: Referral Information, Patient Information, Status, Diagnosis, Test Required, Other notes, Electronic Signature, Attached Documents, Correspondence. Correspondence may be added through a secure channel regarding a specific referral using the ADD CORRESPONDENCE link (FIG. 3f). The correspondence is time stamped for tracking purposes/historic auditing. After a referral has been completed, the office can move it from the Dashboard (active referrals list) to ARCHIVE FIG. 3g (listing of recently completed referrals). Follow-up notes can be added to referrals after they have been archived.

Sending a referral uses CREATE REFERRAL feature in the Main Navigation Bar. Step 1 includes inputting basic information, FIG. 3h. Step 2 includes patient information, FIG. 3i. Step 3 includes Doctor Information, FIG. 3j. Step 4 includes Adding Documents, FIGS. 3k-3o. Step 5 includes Preview and Send, FIG. 3p. Step 6 includes Confirmation Screen, FIG. 3q. The system provides for scheduling a referral, FIG. 3r. After receiving a new referral, the recipient office can SCHEDULE (FIG. 3r-3s), ACCEPT (no appointment needed) (FIG. 3v), or REJECT (FIG. 3t-3u).

The system provides a users list to search by specialty or group name. The main office administrator for the system may add, modify, and delete users. Insurance preferences may be managed with the system (FIGS. 3w-3z and 3aa-3bb).

The Lab Dashboard includes the lab section of the system (FIG. 3cc). Sending a lab request is similar to sending a referral. The user selects CREATE LAB REQUEST then proceeds through the following steps: Step 1 Start (basic information), FIG. 3dd. Step 2 Patient Information, FIG. 3ee. Step 3 Select Lab, FIG. 3ff. Step 4 Select Tests, FIG. 3gg-3ii. Step 5 Preview and Send, FIG. 3jj. Step 6 Confirmation Page, FIG. 3kk.

Figure 3L:
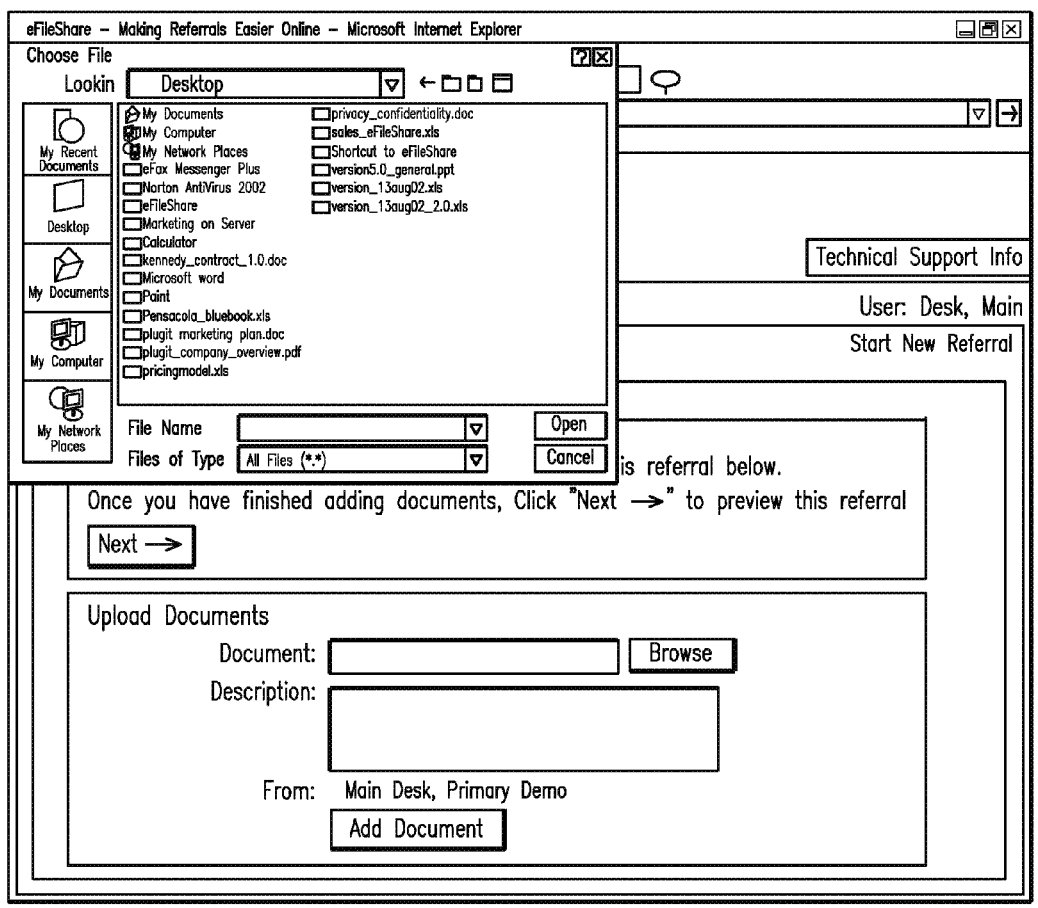
Figure 3R:
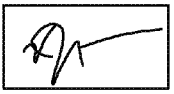
Figure 3T:
Figure 3V:
Figure 3N:
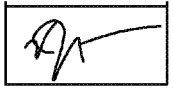

Turning now to FIGS. 3LL-3mm, lab requests may be searched with the system by name, SSN, etc. The Lab section gives the doctor's office the ability to send lab tests(s) requests to a local lab. Usually the lab request is sent from a doctor's office to a specific lab—however sometimes the lab request is not sent to a specific lab. The doctor's office needs to have a record of the lab requests that they have sent out. After the doctor's office has received the results they can archive the lab request. The lab section solves the following problems: patients without test requisition forms showing up at the lab; calls back to the doctor's office to find out what the patient needs, receiving managing and tracking of faxed lab test requisitions from doctor's offices, continuum of care, liability issues, minimizing phone calls and faxes to lab. The lab section also provides the ability to create favorites.

A system for managing the removal of referral from the dashboard is provided. The auto-removal bases the archiving on the status with different parameters. For example, if STATUS SCHEDULED NOTIFIED then Sender—auto archive after X days (e.g., 7) and Recipient—drops from screen X days after marking referral as "Scheduled—notified"; if STATUS SCHEDULED NOT NOTIFIED then Sender—manual archive and Recipient—after sender manually archives; if STATUS ACCEPTED then Sender—manual archive and Recipient—after sender manually archives the referral or it is auto archived after X days; if REJECTED then Sender—manual archive and Recipient—immediately after marking referral as "rejected".

The invention further includes additional features directed to geographic region/markets. While there is a national need to develop a networked system for sharing patient information, health care is often practiced on a local level. To meet these local needs, the following system describes an implementation of a local health information system as part of a national system.

On the local level, the participants in the system would most likely include: physicians, hospitals, pharmacies, labs, and patients. These participants are the same regardless of geographic location. The system of the present invention allows for all of the previously mentioned groups to share information during transfer and authentication mechanisms to limit access to appropriate parties.

Figure 11A:
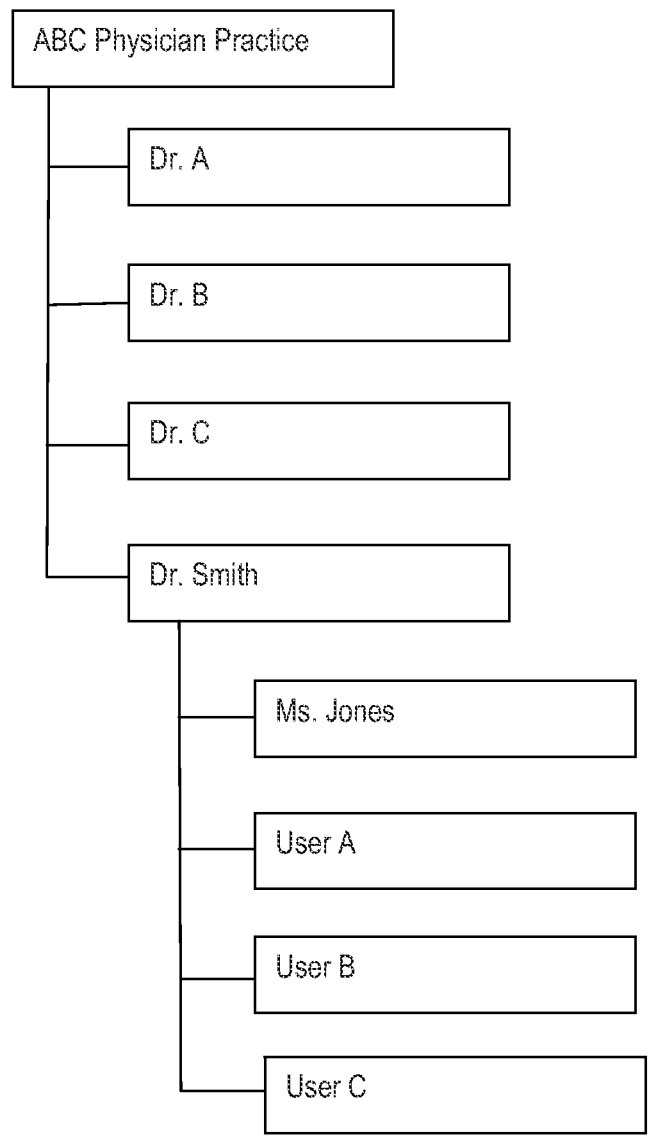
FIGS. 11a and 11b show relationship models for the present invention.

All users would be tied to a geographic market. Initially, the user relationship was based upon the office that they were associated with. Associated with each office were physicians and users. For example, FIG. 11a shows Office, Physicians, and Users. In particular, the Office—ABC Physician Practice has Drs. A, B, C, and Smith associated therewith. Dr. Smith has users A, B, C, and Ms. Jones associated therewith. In this relationship model there could be an unlimited number of offices, physicians, and users.

Figure 11B:
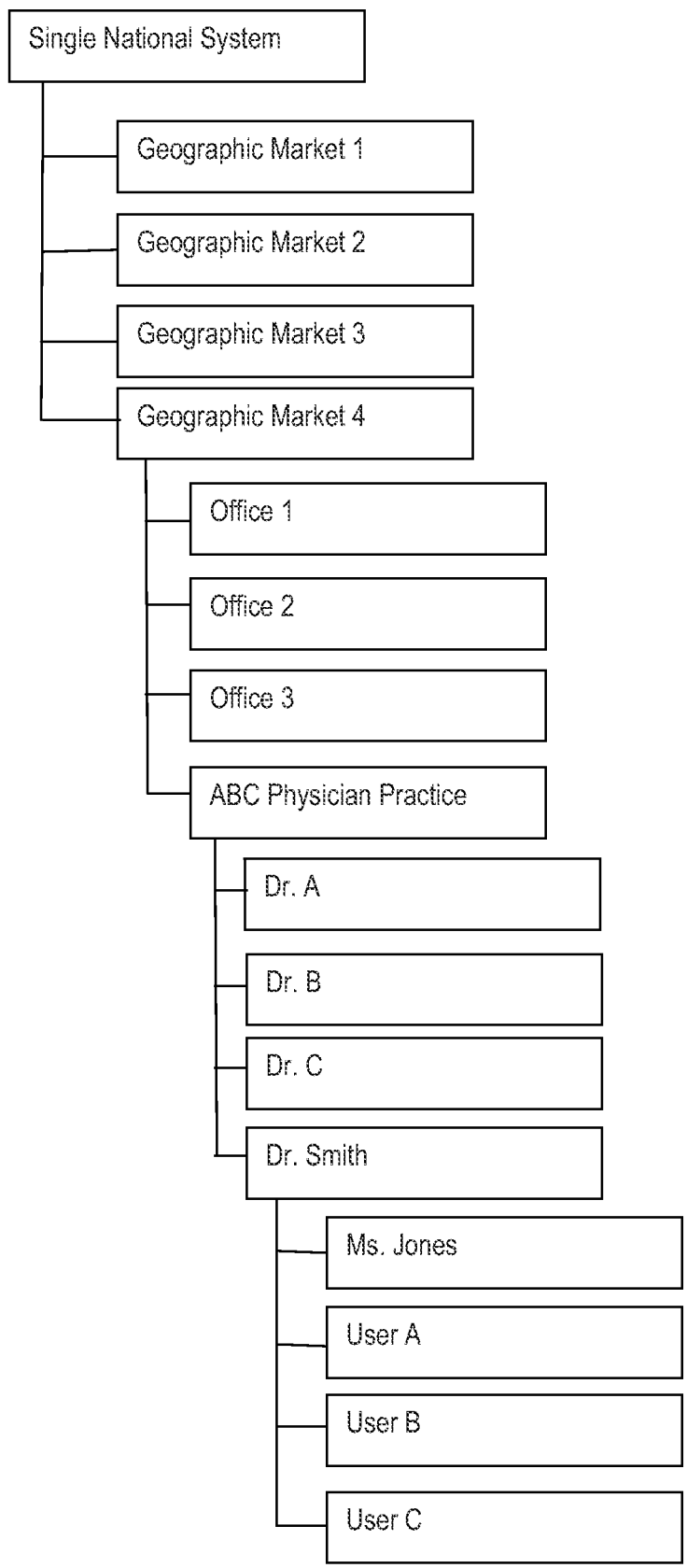

Under an alternative model, a new relationship is introduced wherein all offices are tied to a geographic market as shown in FIG. 11b. As with office, physicians, and users, the number of geographic markets is unlimited. The geographic model may follow the Metropolitan Statistical Area (MSA) standard. Alternately, the geographic market can follow a more realistic model based on the concept that health care is practiced locally and the local perception may deviate from the MSA model. The sample model in FIG. 11b shows a Single National System with Geographic Markets 1-4 associated therewith, Under Geographic Market 4 there are Offices 1, 2, 3, and ABC Physician Practice. Under ABC Physician Practice we have Drs. A, B, C, and Dr. Smith. Finally, under Dr. Smith, we have Users A, B, C, and Ms. Jones. For a user to pass information to another user in a different market, the user needs only to "switch markets" on the first step of the file transfer wizard. Changing markets gives the user access to any other office/physician/user in the entire system.

Figure 12A:

FIGS. 12a and 12b are sample screen displays including the Market Selector box with a drop down list whereby the user can select any market in the system and change markets.

By building a system of networked geographic markets, the invention accomplishes two important tasks. First, it allows health care providers to practice medicine locally. Second, it integrates all users into a national system that allows for information sharing between providers regardless of physical location/market.

The advantages of the invention are numerous, including security, efficiency, auditability, management, and community medical network. Specifically, the invention is more secure for transferring confidential patient information than the phone/fax system since the system only allows authorized users to access the system. Furthermore, the system guides the user through the sending process and ensures that the right physician receives the patient file every time. The invention is also efficient as compared to the phone/fax method since it reduces the time users spend playing "phone tag", waiting on hold, faxing, re-faxing documents related to transferring patient files. The invention also is better for documentation than the phone/fax method since it has automatic, mirrored audit trail system that lets both the sender and recipient know the status of the patient file at all times and documents the entire process by date and time stamping the record at each main status change and also recording and time-stamping all correspondence between offices during the process. The invention is better for managing multiple file transfers since all patient files being sent or received can be managed from a single "dashboard" that shows status on summary information on each file. Finally, the invention provides a secure community medical network for transferring files between every provider in a given market or for that matter transferring files between geographic markets.

It will be readily appreciated that the principles of the invention may apply to other computer applications, such as other mainframes, minicomputers, network servers, supercomputers, personal computers, or workstations, as well as other electronics applications. Therefore, while the discussion herein focuses on a particular application, it should be understood that the invention is not limited to the particular hardware designs, software designs, communications protocols, performance parameters, or application-specific functions disclosed herein.

The invention can also be embodied as computer readable code on a computer readable medium. The computer readable medium is any data storage device that can store data which thereafter can be read by a computer system. Examples of computer readable medium include read-only memory, random-access memory, CD-ROMs, magnetic tape, optical data storage devices. The computer readable medium can also be distributed over network coupled computer systems so that the computer readable code is stored and executed in a distributed fashion.

Based on the foregoing specification, the invention may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the invention. The computer readable media may be, for example, a fixed (hard) drive, diskette, optical disk, magnetic tape, semiconductor memory such as read-only memory (ROM), etc., or any transmitting/receiving medium such as the Internet or other communication network or link. The article of manufacture containing the computer code may be made and/or used by executing the code directly from one medium, by copying the code from one medium to another medium, or by transmitting the code over a network.

An apparatus for making, using or selling the invention may be one or more processing systems including, but not limited to, a central processing unit (CPU), memory, storage devices, communication links and devices, servers, I/O devices, or any sub-components of one or more processing systems, including software, firmware, hardware or any combination or subset thereof, which embody the invention as set forth in the claims.

User input may be received from the keyboard, mouse, pen, voice, touch screen, or any other means by which a human can input data to a computer, including through other programs such as application programs.

One skilled in the art of computer science will easily be able to combine the software created as described with appropriate general purpose or special purpose computer hardware to create a computer system or computer sub-system embodying the method of the invention.

It should be understood that the examples and embodiments described herein are for illustrative purposes only and that various modifications or changes in light thereof will be suggested to persons skilled in the art and are to be included within the spirit and purview of this application.

The invention claimed is:

1. A method for secure transfer of a complete electronic patient information record from a sender to a recipient across a communication network, comprising:

(a) displaying on a first computing device of a sender a user interface including a selection for a type of referral comprising a referral request or a lab request, wherein upon receipt of a selection of the type of referral, displaying to the sender predetermined sets of data fields having minimum input requirements for completion of an electronic patient information record for transfer across a communication network from the first computing device of the sender to a second computing device of a recipient, wherein the predetermined sets of data fields depend on the selected type of referral, wherein
  (i) the first set of data fields comprises fields for receiving initial data for security,
  (ii) the second set of data fields comprises fields for receiving patient specific data identifying a patient, and
  (iii) the third set of data fields comprises fields for receiving recipient data identifying a recipient;
(b) receiving by the first computing device via the user interface input from the sender comprising initial data input, patient specific data input, and recipient data input in each of the respective data fields displayed based on the type of referral request;
(c) saving the initial data input, the patient specific data input, and the recipient data input collectively in the electronic patient information record; and
(d) determining by the first computing device whether the minimum input requirements for completion of the electronic patient information record comprising at least initial data input, patient specific data input, and recipient data input based on the type of referral request has been satisfied wherein at least a predetermined number of the data fields in each of the first, second, and third set are marked as required fields and comprise minimum input requirements for completion of the electronic patient information record, wherein the minimum input requirements for patient specific input comprise at least completion of patient identification and insurance identification fields, and wherein the minimum input requirements for recipient data comprise at least completion of fields for sender, recipient, and diagnosis,
(e) providing a notice that the electronic patient information record is ready to be sent and sending the patient information record across a communication network from the first computing device of the sender to the second computing device of the recipient only after the minimum input requirements for completion of the electronic patient information record is satisfied based on the type of referral request.

2. The method of claim 1 wherein the set of initial data fields comprise fields for patient social security number, priority, scheduling options, referral authorization information number, and specialty/modality, wherein at least a predetermined number of the initial data fields comprise minimum input requirements for completion of the electronic patient information record.

3. The method of claim 1 wherein the set of patient specific data fields comprise fields for last name, first name, date of birth, gender, and primary insurance and phone, wherein at least a predetermined number of the patient specific data fields comprise minimum input requirements for completion of the electronic patient information record.

4. The method of claim 1 wherein the set of recipient data fields comprise fields for sender, recipient, diagnosis codes, and diagnosis notes, wherein at least a predetermined number of the recipient data fields comprise minimum input requirements for completion of the electronic patient information record.

5. The method of claim 1 further comprising storing of an audit trial comprising applying date and time stamps to the electronic patient information record for the transfer.

6. The method of claim 1 further comprising updating a status monitor on one or both of the first computing device of the sender and the second computing device of the recipient that displays a status of the transfer of the electronic patient information record.

7. The method of claim 1 further comprising attaching additional electronic files to the electronic patient information record.

8. The method of claim 1 further comprising additional data fields for receiving input of a selected geographic market, wherein upon receiving input of a selection of the geographic market, certain data fields that are associated with the geographic market are updated to be restricted to that geographic market including restricting available recipients in the recipient data field.

9. A system for secure transfer of a complete electronic patient information record from a sender to a recipient across a communication network, comprising:
  a first computing device associated with a sender in communication across a communications network with a second computing device of a recipient, wherein the first computing device is programmed to:
    (a) display a user interface including a selection for a type of referral comprising a referral request or a lab request, wherein upon receipt of a selection of the type of referral, displaying to the sender predetermined sets of data fields having minimum input requirements for completion of an electronic patient information record for transfer across a communication network from the first computing device of the sender to a second computing device of a recipient, wherein the predetermined sets of data fields depend on the selected type of referral, wherein
      (i) the first set of data fields comprises fields for receiving initial data for security,
      (ii) the second set of data fields comprises fields for receiving patient specific data identifying a patient, and
      (iii) the third set of data fields comprises fields for receiving recipient data identifying a recipient;
    (b) receive via the user interface input from the sender comprising initial data input, patient specific data input, and recipient data input in each of the respective data fields displayed based on the type of referral request;
    (c) save the initial data input, the patient specific data input, and the recipient data input collectively in the electronic patient information record; and
    (d) determine whether the minimum input requirements for completion of the electronic patient information record comprising at least initial data input, patient specific data input, and recipient data input based on the type of referral request has been satisfied wherein at least a predetermined number of the data fields in each of the first, second, and third set are marked as required fields and comprise minimum input requirements for completion of the electronic patient information record, wherein the minimum input requirements for patient specific input comprise at least completion of patient identification and insurance identification fields, and wherein the minimum input requirements for recipient data comprise at least completion of fields for sender, recipient, and diagnosis and
    (e) providing a notice that the electronic patient information record is ready to be sent and sending the patient information record across a communication network from the first computing device of the sender to the second computing device of the recipient only after the minimum input requirements for completion of the electronic patient information record is satisfied based on the type of referral request.

10. The system of claim 9 wherein the set of initial data fields comprise fields for patient social security number, priority, scheduling options, referral authorization information number, and specialty/modality, wherein at least a predetermined number of the initial data fields comprise minimum input requirements for completion of the electronic patient information record.

11. The system of claim 9 wherein the set of patient specific data fields comprise fields for last name, first name, date of birth, gender, and primary insurance and phone, wherein at least a predetermined number of the patient specific data fields comprise minimum input requirements for completion of the electronic patient information record.

12. The system of claim 9 wherein the set of recipient data fields comprise fields for sender, recipient, diagnosis codes, and diagnosis notes, wherein at least a predetermined number of the recipient data fields comprise minimum input requirements for completion of the electronic patient information record.

13. The system of claim 9 wherein the first computing device is further programmed to store of an audit trial comprising applying date and time stamps to the electronic patient information record for the transfer.

14. The system of claim 9 wherein the first computing device is further programmed to update a status monitor on the first computing device of the sender that displays a status of the transfer of the electronic patient information record.

15. The system of claim 9 wherein the first computing device is further programmed to attach additional electronic files to the electronic patient information record.

16. The system of claim 9 wherein the first computing device is further programmed to display additional data fields for receiving input of a selected geographic market, wherein upon receiving input of a selection of the geographic market, certain data fields that are associated with the geographic market are updated to be restricted to that geographic market including restricting available recipients in the recipient data field.

17. A tangible computer readable media containing program instructions for secure transfer of a complete electronic patient information record from a sender to a recipient across a communication network, said computer readable media comprising computer code devices for:
(a) displaying on a first computing device of a sender a user interface including a selection for a type of referral comprising a referral request or a lab request, wherein upon receipt of a selection of the type of referral, displaying to the sender predetermined sets of data fields having minimum input requirements for completion of an electronic patient information record for transfer across a communication network from the first computing device of the sender to a second computing device of a recipient, wherein the predetermined sets of data fields depend on the selected type of referral, wherein
(i) the first set of data fields comprises fields for receiving initial data for security,
(ii) the second set of data fields comprises fields for receiving patient specific data identifying a patient, and
(iii) the third set of data fields comprises fields for receiving recipient data identifying a recipient;
(b) receiving by the first computing device via the user interface input from the sender comprising initial data input, patient specific data input, and recipient data input in each of the respective data fields displayed based on the type of referral request;
(c) saving the initial data input, the patient specific data input, and the recipient data input collectively in the electronic patient information record;
(d) determining by the first computing device whether the minimum input requirements for completion of the electronic patient information record comprising at least initial data input, patient specific data input, and recipient data input based on the type of referral request has been satisfied wherein at least a predetermined number of the data fields in each of the first, second, and third set are marked as required fields and comprise minimum input requirements for completion of the electronic patient information record, wherein the minimum input requirements for patient specific input comprise at least completion of patient identification and insurance identification fields, and wherein the minimum input requirements for recipient data comprise at least completion of fields for sender, recipient, and diagnosis, and
(e) providing a notice that the electronic patient information record is ready to be sent and sending the patient information record across a communication network from the first computing device of the sender to the second computing device of the recipient only after the minimum input requirements for completion of the electronic patient information record is satisfied based on the type of referral request.

18. The computer readable media of claim 17 wherein the set of initial data fields comprise fields for patient social security number, priority, scheduling options, referral authorization information number, and specialty/modality, wherein at least a predetermined number of the initial data fields comprise minimum input requirements for completion of the electronic patient information record.

19. The computer readable media of claim 17 wherein the set of patient specific data fields comprise fields for last name, first name, date of birth, gender, and primary insurance and phone, wherein at least a predetermined number of the patient specific data fields comprise minimum input requirements for completion of the electronic patient information record.

20. The computer readable media of claim 17 wherein the set of recipient data fields comprise fields for sender, recipient, diagnosis codes, and diagnosis notes, wherein at least a predetermined number of the recipient data fields comprise minimum input requirements for completion of the electronic patient information record.

* * * * *